(12) United States Patent
Heil et al.

(10) Patent No.: US 8,334,058 B2
(45) Date of Patent: Dec. 18, 2012

(54) COMPOUNDS FOR ORGANIC ELECTRONIC DEVICES

(75) Inventors: Holger Heil, Darmstadt (DE); Philipp Stoessel, Frankfurt am Main (DE); Horst Vestweber, Gilserberg (DE); Rocco Fortte, Frankfurt (DE)

(73) Assignee: Merck Patent GmbH, Darmstadt (DE)

( * ) Notice: Subject to any disclaimer, the term of this patent is extended or adjusted under 35 U.S.C. 154(b) by 757 days.

(21) Appl. No.: 11/911,356

(22) PCT Filed: Mar. 20, 2006

(86) PCT No.: PCT/EP2006/002531
§ 371 (c)(1),
(2), (4) Date: Oct. 12, 2007

(87) PCT Pub. No.: WO2006/108497
PCT Pub. Date: Oct. 19, 2006

(65) Prior Publication Data
US 2008/0145708 A1 Jun. 19, 2008

(30) Foreign Application Priority Data
Apr. 14, 2005 (EP) .................................. 05008130

(51) Int. Cl.
*H01L 51/50* (2006.01)

(52) U.S. Cl. ........ 428/690; 428/917; 313/504; 313/505; 313/506; 257/40; 257/E51.05; 257/E51.026; 257/E51.032; 528/394; 528/397; 528/422

(58) Field of Classification Search .................. 428/690, 428/917; 313/504, 505, 506; 257/40, E51.05, 257/E51.026, E51.032; 528/394, 397, 422
See application file for complete search history.

(56) References Cited

U.S. PATENT DOCUMENTS

| | | | |
|---|---|---|---|
| 5,840,217 A | 11/1998 | Lupo et al. | |
| 6,300,502 B1 * | 10/2001 | Kannan et al. | 548/156 |
| 2002/0121860 A1 * | 9/2002 | Seo et al. | 313/506 |
| 2003/0008174 A1 | 1/2003 | Suzuki et al. | |
| 2003/0072966 A1 | 4/2003 | Hosokawa et al. | |
| 2003/0087126 A1 | 5/2003 | Ishida et al. | |
| 2004/0253389 A1 | 12/2004 | Suzuki et al. | |
| 2005/0137245 A1 | 6/2005 | Hudkins et al. | |
| 2005/0221124 A1 * | 10/2005 | Hwang et al. | 428/690 |
| 2005/0221274 A1 | 10/2005 | Negulescu et al. | |
| 2006/0166034 A1 | 7/2006 | Saitoh et al. | |
| 2007/0170419 A1 | 7/2007 | Gerhard et al. | |
| 2008/0125609 A1 | 5/2008 | Vestweber et al. | |
| 2009/0066225 A1 | 3/2009 | Kimura et al. | |
| 2010/0033081 A1 | 2/2010 | Yamada et al. | |

FOREIGN PATENT DOCUMENTS

| | | |
|---|---|---|
| EP | 1061112 A1 | 12/2000 |
| EP | 1221434 A1 | 7/2002 |
| EP | 1491568 A1 | 12/2004 |
| JP | 1118409 | 5/1989 |
| JP | 6-192654 A | 7/1994 |
| JP | 7-278537 A | 10/1995 |
| JP | 11-144875 * | 5/1999 |
| JP | 11184109 | 7/1999 |
| JP | 2001-131541 A | 5/2001 |
| JP | 2002-154993 A | 5/2002 |
| JP | 2002-329582 A | 11/2002 |
| JP | 2003238516 | 8/2003 |
| JP | 2003-261473 A | 9/2003 |
| JP | 2004-083481 A | 3/2004 |
| JP | 2004-091350 A | 3/2004 |
| JP | 2004-292743 A | 10/2004 |
| JP | 2005-082702 A | 3/2005 |
| JP | 2007-119454 A | 5/2007 |
| JP | 2007-526634 A | 9/2007 |
| JP | 2007-526909 A | 9/2007 |
| JP | 2008-019238 A | 1/2008 |
| JP | 2008521857 A | 6/2008 |
| JP | 2009-524701 A | 7/2009 |
| JP | 11-144875 A | 2/2012 |
| WO | WO-2004/020387 A1 | 3/2004 |
| WO | WO-2004/061047 A2 | 7/2004 |
| WO | WO-2006/100896 A1 | 9/2006 |
| WO | WO-2007/086701 A1 | 8/2007 |

OTHER PUBLICATIONS

English Translation of JP 11-144875.*
Kannan et al., "Toward Highly Active Two-Photon Absorbing Liquids. Synthesis and Characterization of 1,3,5-Triazine-Based Octupolar Molecules", *Chem. Mater.*, vol. 16, pp. 185-194 (2004).
Hellwinkel et al., "Palladiumacetat-vermittelte Cyclisierung von di- und tri-funktionellen Triarylaminen, Diarylethern und Diarylketonen", *Liebigs An. Chem.*, pp. 945-949 (1989).
Lin et al., "Tanins and Related Compounds, CII. Structures of Terchebulin, an Ellatitamin Having a Novel Tetraphenylcarboxylic Acid (Terchebolic Acid) Moiety, and Biogenetically Related Tannins from Termlnalia chebula Retz", *Chem. Pharm. Bull.*, No. 38, vol. 11, pp. 3004-3008 (1990).
White, et al., "Ageing of SRC-II middle distillate from Illinois No. 6 coal", *FUEL*, vol. 62, pp. 1397-1403 (1983).

* cited by examiner

*Primary Examiner* — D. Lawrence Tarazano
*Assistant Examiner* — Gregory Clark
(74) *Attorney, Agent, or Firm* — Connolly Bove Lodge & Hutz LLP

(57) ABSTRACT

The present invention relates to the improvement of organic electroluminescent devices, in particular blue-emitting devices, by using compounds of the formula (1) as dopants in the emitting layer.

23 Claims, No Drawings

COMPOUNDS FOR ORGANIC ELECTRONIC DEVICES

RELATED APPLICATIONS

This application is a national stage application (under 35 U.S.C. §371) of PCT/EP2006/002531, filed Mar. 20, 2006, which claims benefit of European application 05008130.6, filed Apr. 14, 2005.

The present invention describes novel compounds and the use thereof in organic electronic devices.

The use of semiconducting organic compounds which are capable of emission of light in the visible spectral region in organic electroluminescent devices (OLEDs) is known. The general structure of such devices is described, for example, in U.S. Pat. No. 4,539,507, U.S. Pat. No. 5,151,629, EP 0676461 and WO 9827136.

However, these devices still exhibit considerable problems which require urgent improvement:
1. The efficiency, especially in the case of fluorescent OLEDs, is still too low and must be improved.
2. The operative lifetime is still low, in particular in the case of blue emission, meaning that it has hitherto only been possible to achieve simple applications commercially.
3. The operating voltage is quite high, especially in the case of fluorescent OLEDs, and should therefore be further reduced in order to improve the power efficiency. This is of particularly great importance for mobile applications. In particular, OLEDs in accordance with the prior art exhibit a strong dependence of the operating voltage on the layer thickness of the hole-transport layer.
4. Many blue-emitting emitters which comprise both aromatic amines and also double-bond systems are thermally unstable and decompose on sublimation or on vapour deposition. The use of these systems is consequently only possible with great losses and with high technical complexity, if at all.

As closest prior art, the use of certain arylvinylamines by Idemitsu (for example WO 04/013073, WO 04/016575, WO 04/018587) can be mentioned. Very good lifetimes with dark-blue emission are cited therewith. However, these results are highly dependent on the host material used, meaning that the lifetimes cited cannot be compared as absolute values, but instead always only on use in an optimised system. Furthermore, these compounds are thermally unstable and cannot be evaporated without decomposition, which therefore requires high technical complexity for the OLED production and thus represents a significant technical disadvantage. A further disadvantage is the emission colour of these compounds. While Idemitsu cites dark-blue emission (CIE y coordinates in the range 0.15-0.18), it has not been possible to reproduce these colour coordinates in simple devices in accordance with the prior art. On the contrary, green-blue emission is obtained here. It is not clear how blue emission can in fact be produced using these compounds.

There thus continues to be a demand for blue-emitting compounds which result in good efficiencies in organic electroluminescent devices and at the same time result in long service lives and can be processed without technical problems. Surprisingly, it has now been found that organic electroluminescent devices which comprise certain compounds—mentioned below—as blue-emitting dopants in a host material have significant improvements over the prior art. It is possible with these materials to obtain longer service lives at the same time as higher efficiency. In addition, these compounds can, in contrast to materials in accordance with the prior art, be sublimed without notable decomposition, even in relatively large amounts, and are therefore significantly easier to handle than materials in accordance with the prior art.

Furthermore, these compounds are suitable for use as hole-transport material, as electron-transport material or as matrix material for phosphorescent devices. The present invention therefore relates to these compounds and to the use thereof in OLEDs.

The invention relates to compounds of the formula (1)

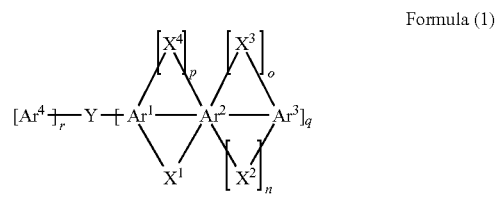

Formula (1)

where the following applies to the symbols and indices used:

Y is on each occurrence N, P, P=O, $PF_2$, P=S, As, As=O, As=S, Sb, Sb=O, Sb=S, C—O, O, S, Se, Te, SO, $SO_2$, Se=O, $SeO_2$, Te=O or $TeO_2$;

$Ar^1$, $Ar^2$, $Ar^3$ is on each occurrence, identically or differently, an aryl or heteroaryl group having 5 to 24 aromatic ring atoms, which may be substituted by one or more radicals $R^1$;

$Ar^4$ is on each occurrence, identically or differently, an aromatic or heteroaromatic ring system having 5 to 40 aromatic ring atoms, which may be substituted by one or more radicals $R^1$;

$R^1$ is on each occurrence, identically or differently, H, F, Cl, Br, I, CN, $NO_2$, $Si(R^2)_3$, a straight-chain alkyl, alkoxy or thioalkoxy group having 1 to 40 C atoms or a branched or cyclic alkyl, alkoxy or thioalkoxy group having 3 to 40 C atoms, each of which may be substituted by one or more radicals $R^2$, where one or more non-adjacent $CH_2$ groups may be replaced by —$R^2COR^2$—, —C↑C—, $Si(R^2)_2$, $Ge(R^2)_2$, $Sn(R^2)_2$, C=O, C=S, C=Se, C=$NR^2$, —O—, —S— or —$CONR^2$— and where one or more H atoms may be replaced by F, Cl, Br, I, CN or $NO_2$, or an aromatic or heteroaromatic ring system having 5 to 40 aromatic ring atoms, which may be substituted by one or more radicals $R^2$, or an aryoxy or heteroaryloxy group having 5 to 40 aromatic ring atoms, which may be substituted by one or more radicals $R^2$, or a combination of these systems; two or more substituents $R^1$ here may also with one another form a mono- or polycyclic aliphatic ring system;

$R^2$ is on each occurrence, identically or differently, H or an aliphatic or aromatic hydrocarbon radical having 1 to 20 C atoms;

$X^1$, $X^4$ is on each occurrence, identically or differently, a bridge which, with $Ar^1$ and $Ar^2$, defines a cyclic system, selected from $B(R^1)$, $C(R^1)_2$, $Si(R^1)_2$, C=O, C=$NR^1$, C=$C(R^1)_2$, O, S, S=O, $SO_2$, $N(R^1)$, $P(R^1)$, P(=O)$R^1$, P(=S)$R^1$ or a combination of two, three or four of these groups;

$X^2$, $X^3$ is on each occurrence, identically or differently, $X^1$ and, with $Ar^2$ and $Ar^3$, defines a cyclic ring system;

n, o, p is on each occurrence, identically or differently, 0 or 1, with the proviso that, for Y from the fifth main group, n, p and o may only simultaneously be 0 if q=3; n=0 or o=0 or p=0 here means that two H atoms or radicals $R^1$ are present instead of the bridge;

q is 1, 2 or 3 if Y is bonded via an element of the fifth main group, and is 2 if Y is bonded via oxygen, and is 1 or 2 if Y is bonded via another element of the sixth main group;

r is (3-q) if Y is bonded via an element of the fifth main group, and is (2-q) if Y is bonded via an element of the sixth main group;

the following compound is excluded here:

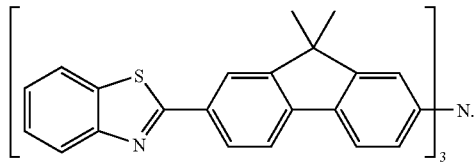

For the purposes of this invention, an aryl group or a heteroaryl group is taken to mean an aromatic group or heteroaromatic group respectively having a common aromatic electron system, where an aryl group contains 6 to 24 C atoms and a heteroaryl group contains 2 to 24 C atoms and a total of at least 5 aromatic ring atoms. The hetero atoms are preferably selected from N, O and/or S. For the purposes of this invention, this can be a single homo- or heterocyclic ring, for example benzene, pyridine, thiophene, etch, or it can be a fused aromatic ring system in which at least two aromatic or heteroaromatic rings, for example benzene rings, are "fused" to one another, i.e. have at least one common edge and thus also a common aromatic system. This aryl or heteroaryl group may be substituted or unsubstituted; any substituents present may likewise form further ring systems. Thus, for example, systems such as naphthalene, anthracene, phenanthrene, pyrene, etc., are regarded as aryl groups for the purposes of this invention and quinoline, acridine, benzothiophene, carbazole, etch, are regarded as heteroaryl groups for the purposes of this invention, while, for example, biphenyl, fluorene, spirobifluorene, etc., are not aryl groups since separate aromatic electron systems are present here.

For the purposes of this invention, an aromatic ring system contains 6 to 40 C atoms in the ring system. For the purposes of this invention, a heteroaromatic ring system contains 2 to 40 C atoms and at least one heteroatom in the ring system, with the proviso that the total number of C atoms and heteroatoms is at least 5. The heteroatoms are preferably selected from N, O and/or S. For the purposes of this invention, an aromatic or heteroaromatic ring system is taken to mean a system which does not necessarily contain only aryl or heteroaryl groups, but in which, in addition, a plurality of aryl or heteroaryl groups may be interrupted by a short, non-aromatic unit (less than 10% of the atoms other than H, preferably less than 5% of the atoms other than H), such as, for example, an $sp^3$-hybridised C, N or O atom. Thus, for example, systems such as 9,9'-spirobifluorene, 9,9-diarylfluorene, triarylamine, diaryl ether, etc., are also to be regarded as aromatic ring systems for the purposes of this invention.

For the purposes of the present invention, a $C_1$- to $C_{40}$-alkyl group, in which individual H atoms or $CH_2$ groups may also be substituted by the above-mentioned groups, is particularly preferably taken to mean the radicals methyl, ethyl, n-propyl, i-propyl, n-butyl, i-butyl, s-butyl, t-butyl, 2-methylbutyl, n-pentyl, s-pentyl, cyclopentyl, n-hexyl, cyclohexyl, n-heptyl, cycloheptyl, n-octyl, cyclooctyl, 2-ethylhexyl, trifluoromethyl, pentafluoroethyl, 2,2,2-trifluoroethyl, ethenyl, propenyl, butenyl, pentenyl, cyclopentenyl, hexenyl, cyclohexenyl, heptenyl, cycloheptenyl, octenyl, cyclooctenyl, ethynyl, propynyl, butynyl, pentynyl, hexynyl or octynyl, A $C_1$- to $C_{40}$-alkoxy group is particularly preferably taken to mean methoxy, ethoxy, n-propoxy, i-propoxy, n-butoxy, i-butoxy, s-butoxy, t-butoxy or 2-methylbutoxy. A $C_2$-$C_{24}$-aryl or -heteroaryl group, which can be monovalent or divalent depending on the use, may also be substituted by the above-mentioned radicals $R^1$ and may be linked to the aromatic or heteroaromatic ring system at any desired positions, is taken to mean, in particular, groups derived from benzene, naphthalene, anthracene, phenanthrene, pyrene, dihydropyrene, chrysene, perylene, fluoranthene, tetracene, pentacene, benzopyrene, furan, benzofuran, isobenzofuran, dibenzofuran, thiophene, benzothiophene, isobenzothiophene, dibenzothiophene, pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, pyrazine, phenazine, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole. For the purposes of this invention, aromatic and heteroaromatic ring systems are taken to mean, for example, biphenylene, terphenylene, fluorene, spirobifluorene, dihydrophenanthrene, tetrahydropyrene and cis- or trans-indenofluorene, in addition to the above-mentioned aryl and heteroaryl groups.

Preference is given to compounds of the formula (1) in which the symbol Y stands for nitrogen, phosphorus, C=O or P=O, particularly preferably for nitrogen, C=O or P=O, very particularly preferably for nitrogen. The choice of the unit Y here depends on the desired function of the compound of the formula (1). If it is intended to employ the compound of the formula (1) as emitter in an emission layer or as hole-transport material, for example in a hole-transport or hole-injection layer, the symbol Y preferably stands for nitrogen or phosphorus, particularly preferably for nitrogen. If it is intended to employ the compound of the formula (1) as matrix material for phosphorescent emitters in an emission layer or as electron-transport and/or hole-blocking material, for example in an electron-transport layer or in a hole-blocking layer, for phosphorescent or fluorescent devices, the symbol Y preferably stands for C=O or for P=O.

Preference is furthermore given to compounds of the formula (1) in which the symbols $Ar^1$, $Ar^2$ and $Ar^3$, identically or differently on each occurrence, stand for an aryl or heteroaryl group having 5 to 16 aromatic ring atoms, which may be substituted by one or two radicals $R^1$, particularly preferably for an aryl or heteroaryl group selected from benzene, naphthalene, anthracene, phenanthrene, pyridine, pyrene and thiophene, in particular benzene, each of which may be substituted by one or two radicals $R^1$.

Particular preference is thus given to compounds of the formula (2)

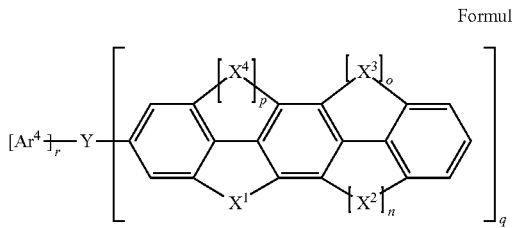

Formula (2)

where the symbols and indices used have the same meaning as described above, and where each of the phenyl and phenylene groups may also be substituted by one or more radicals R¹.

If the phenyl or phenylene groups of the formula (2) are substituted by R¹, the radicals R¹ are preferably bonded in the position as shown in the formula (2a):

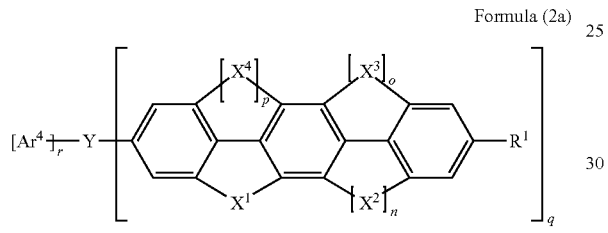

Formula (2a)

Preference is furthermore given to compounds of the formula (1) in which the symbol Ar⁴, identically or differently on each occurrence, stands for an aromatic or heteroaromatic ring system having 5-16 aromatic ring atoms or for spirobifluorene, each of which may be substituted by one or more radicals R¹, particularly preferably for an aromatic or heteroaromatic ring system selected from benzene, naphthalene, anthracene, phenanthrene, pyridine, pyrene and thiophene, in particular benzene, each of which may be substituted by one or two radicals R¹.

Preference is furthermore given to compounds of the formula (1) in which the symbol R¹, identically or differently on each occurrence, stands for H, F, CN, Si(R²)₃, a straight-chain alkyl group having 1 to 5 C atoms or a branched alkyl group having 3 to 5 C atoms, where one or more non-adjacent CH₂ groups may be replaced by Si(R²)₂, —R²C═CR²—, —C≡C—, —O— or —S— and where one or more H atoms may be replaced by F, or a monovalent aryl or heteroaryl group having 5 to 16 aromatic ring atoms, which may be substituted by one or more radicals R², particularly preferably for H, F, CN, Si(Me)₃, methyl, tert-butyl, a phenyl group or a monovalent heteroaryl group having 5 or 6 aromatic ring atoms, each of which may be substituted by one or more radicals R². R¹ is very particularly preferably H if it is bonded directly to one of the groups Ar¹ to Ar⁴. R¹, if it is bonded to the group X¹, X², X³ and/or X⁴, is particularly preferably, identically or differently on each occurrence, methyl, tert-butyl, a phenyl group, which may be substituted by one or more C₁- to C₄-alkyl groups, or a monovalent heteroaryl group having 5 or 6 aromatic ring atoms, which may be substituted by one or more C₁- to C₄-alkyl groups, very particularly preferably methyl or a phenyl group, which may be substituted by one or more C₁- to C₄-alkyl groups. In each case, two or more radicals R¹ may also with one another form a ring system.

Preference is furthermore given to compounds of the formula (1) in which the symbols X¹, X², X³ and X⁴ on each occurrence, identically or differently, are a bridge which, with Ar¹ and Ar² or with Ar² and Ar³, defines a cyclic system, selected from C(R¹)₂, C═O, C═NR¹, O, S, S═, SO₂, N(R¹), P(R¹), P(═O)R¹, C(R¹)₂—C(R¹)₂, C(R¹)₂—C(R¹)₂—C(R¹)₂, C(R¹)₂—O, C(R¹)₂—O—C(R¹)₂. Particular preference is given to compounds of the formula (1) in which the symbols X¹, X², X³ and X⁴ on each occurrence, identically or differently, are selected from C(R¹)₂, N(R¹), P(R¹) and P(═O)(R¹). Very particular preference is given to C(R¹)₂.

Preference is furthermore given to compounds in which p=0 and one of the two indices n and o=1, while the other of the two indices is 0; particularly preferably, p and n=0 and o=1.

Particular preference is thus given to compounds of the formula (3) or of the formula (4)

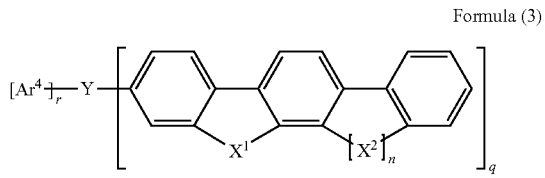

Formula (3)

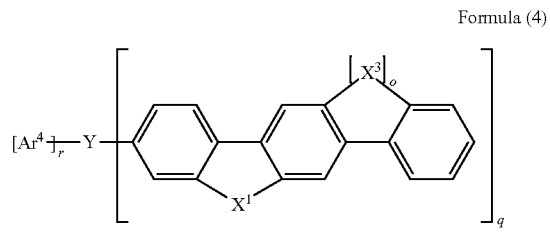

Formula (4)

where the symbols and indices used have the same meaning as described above, and where each of the phenyl and phenylene groups may also be substituted by one or more radicals R¹.

Preference is furthermore given to compounds in which the index q, identically or differently on each occurrence, stands for 2 or 3, very particularly preferably for 3, if Y is selected from the fifth main group. If Y is selected from the sixth main group, the index q is preferably 2.

Particular preference is given to compounds of the formula (1) which have a symmetrical structure and a three-digit axis of rotation if Y is selected from the fifth main group or a two-digit axis of rotation if Y is selected from the sixth main group, which relates not only to the aromatic groups Ar¹ to Ar³, but also to the bridges X¹ to X⁴ and the radicals R¹ and R².

Examples of preferred compounds of the formula (1) are the structures (1) to (82) shown below.

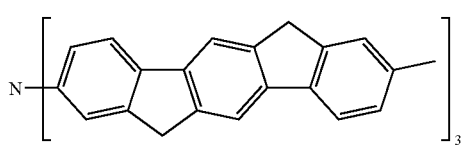 (1)
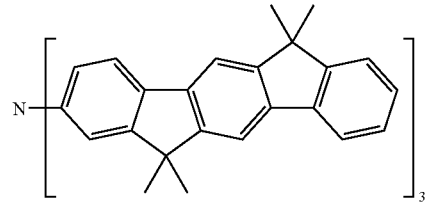 (2)
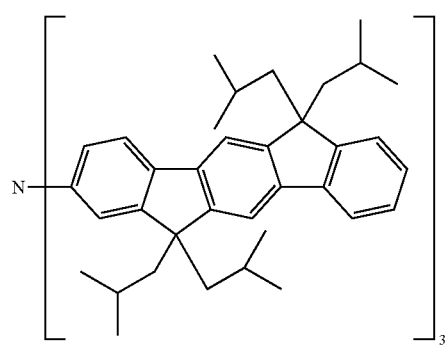 (3)
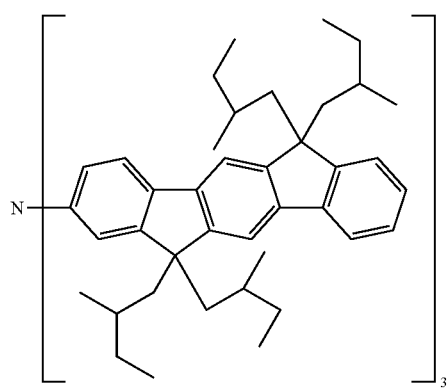 (4)
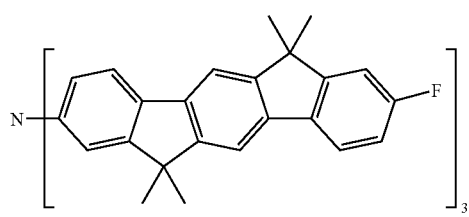 (5)
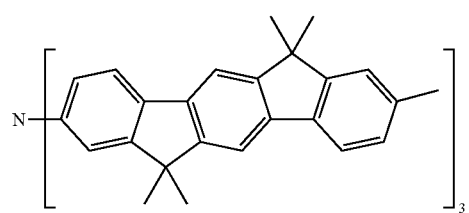 (6)
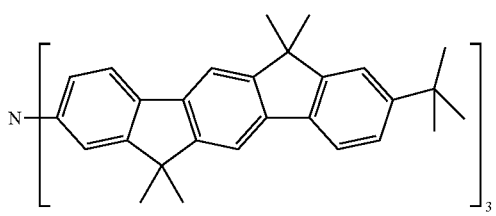 (7)
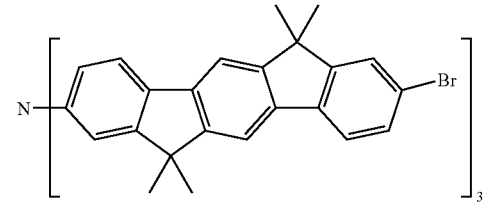 (8)
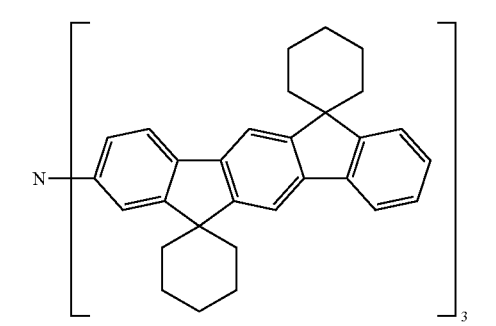 (9)
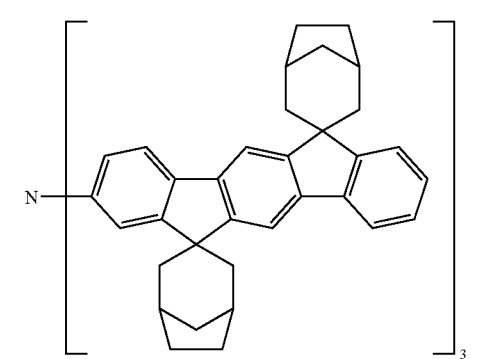 (10)
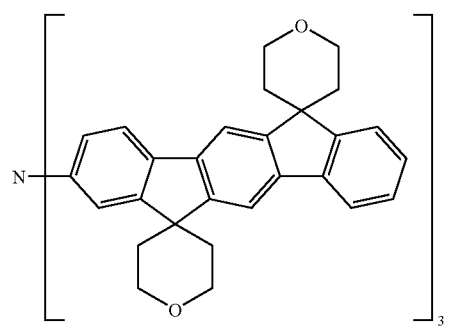 (11)

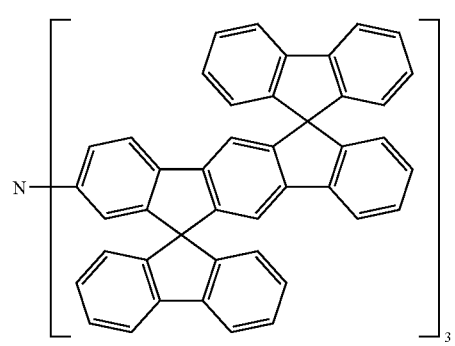
(12)
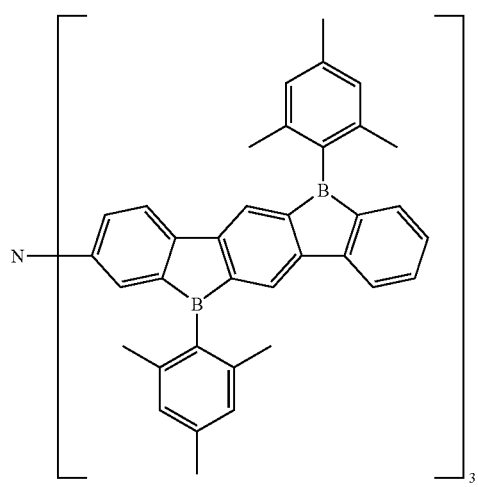
(13)
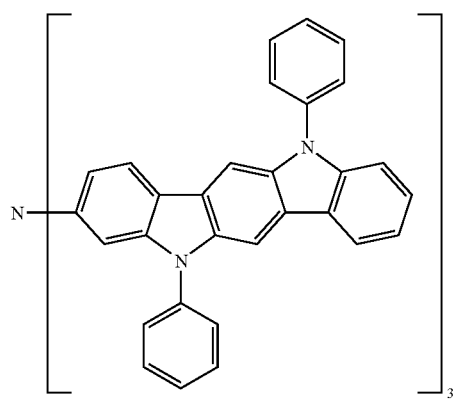
(14)
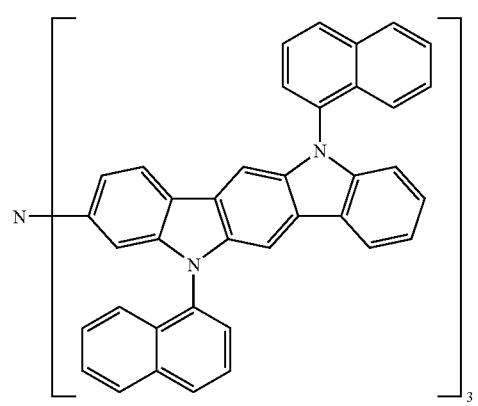
(15)
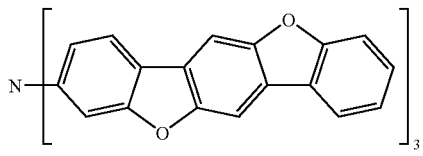
(16)
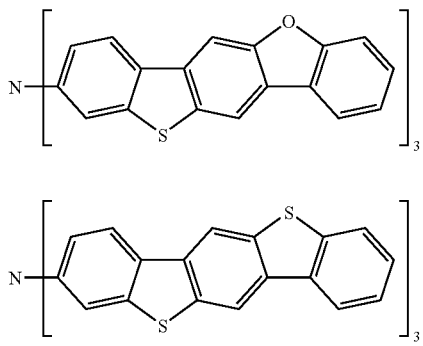
(17)
(18)
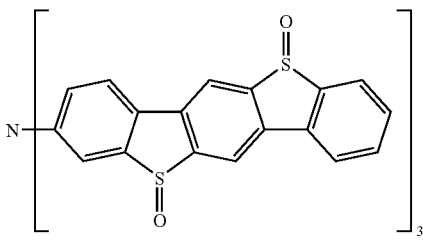
(19)
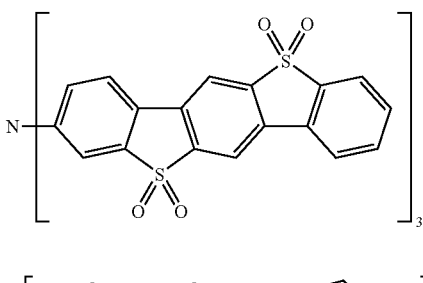
(20)
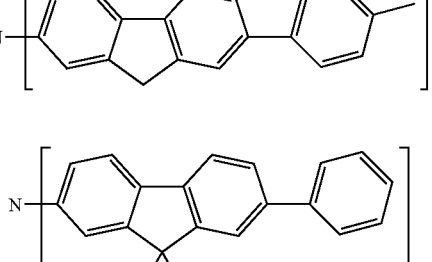
(21)
(22)
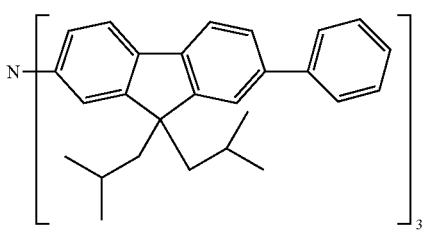
(23)

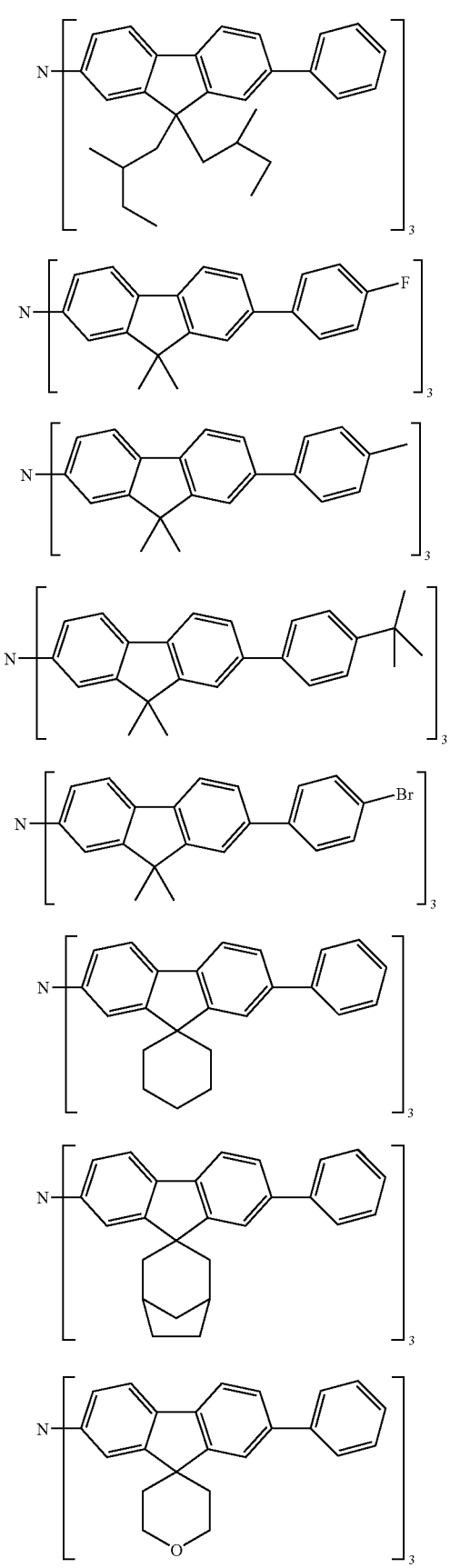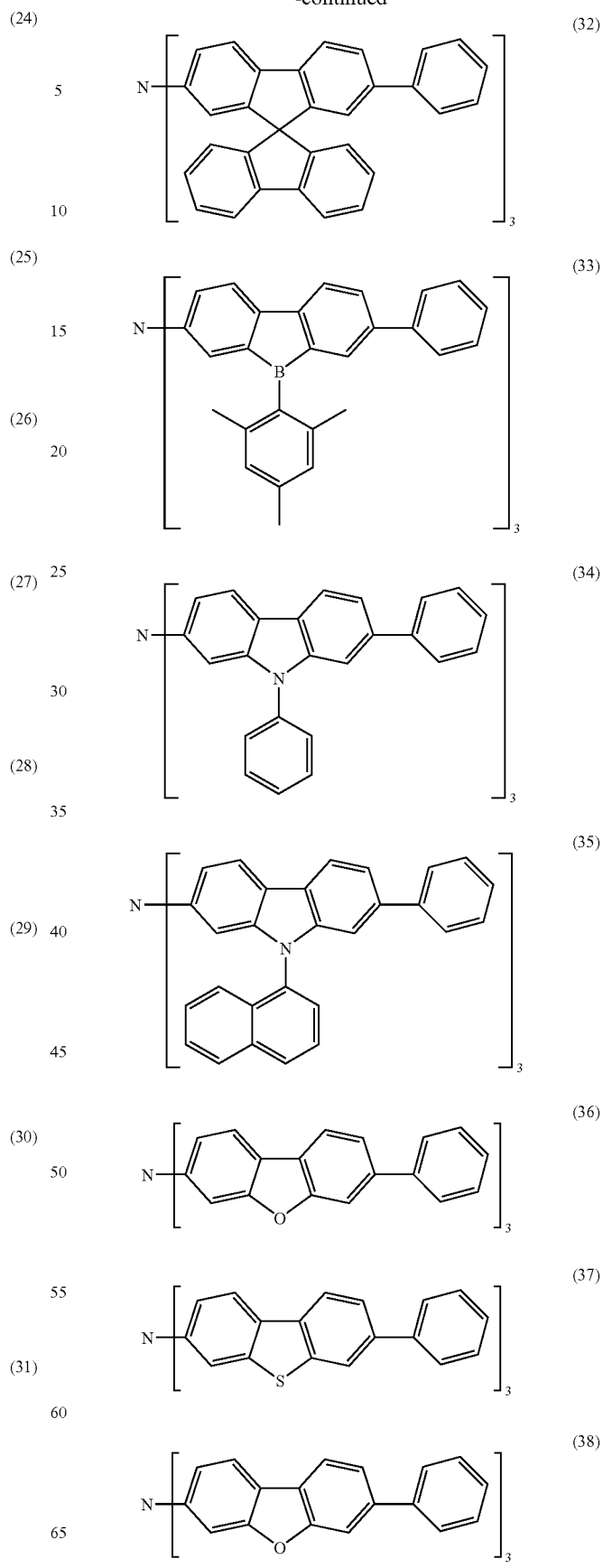

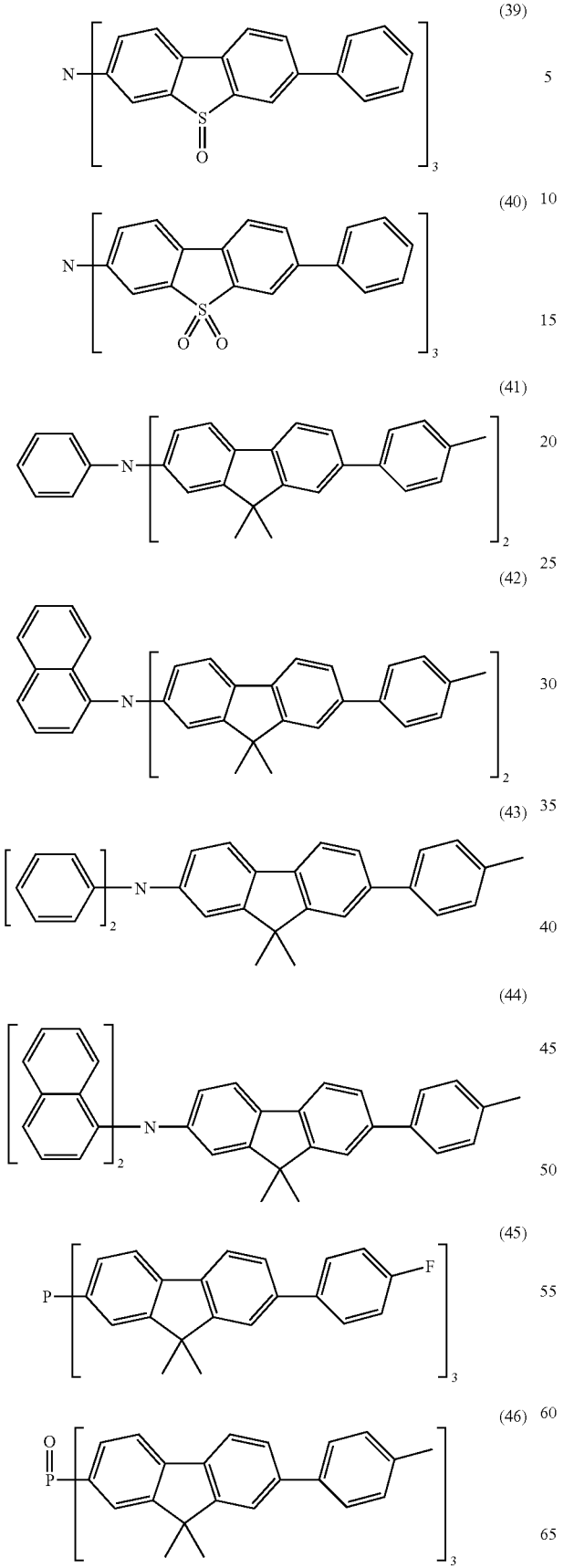
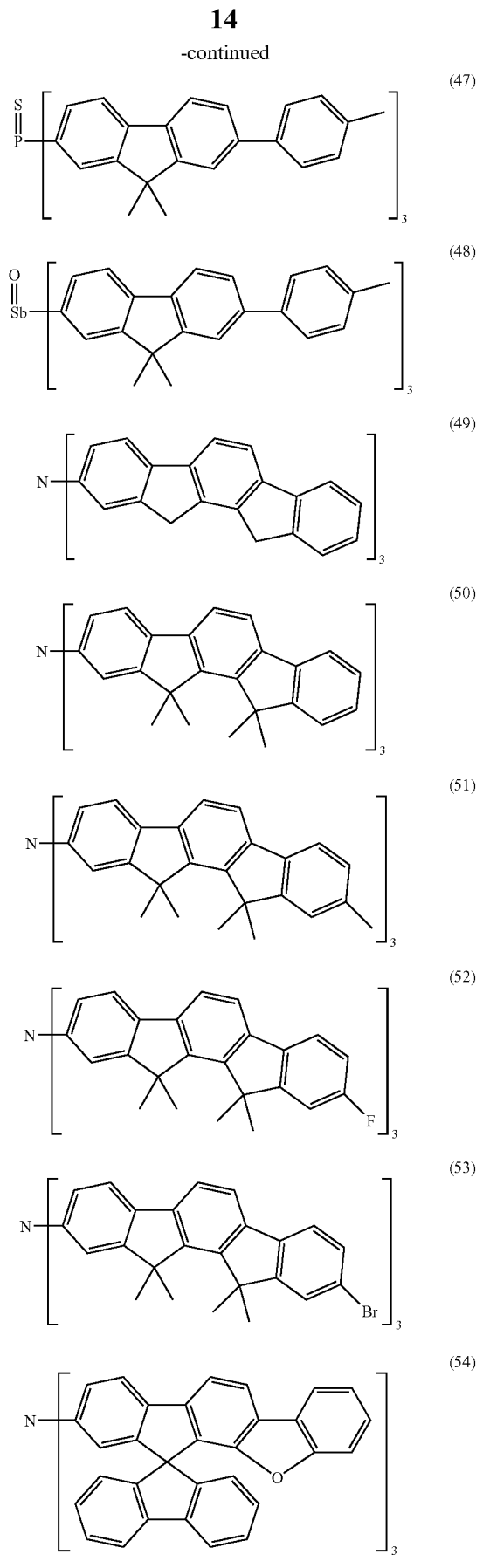

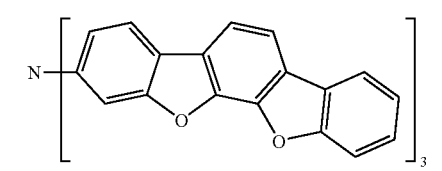(55)
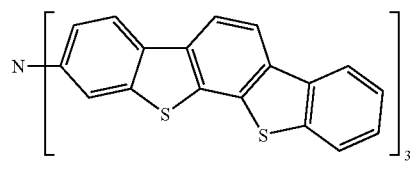(56)
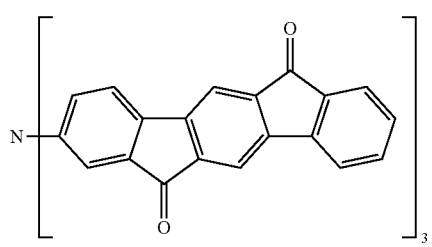(57)
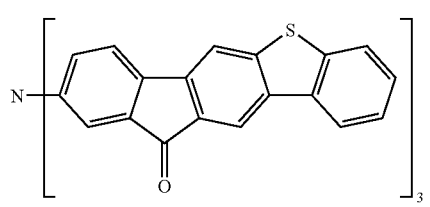(58)
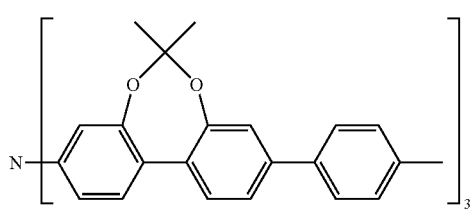(59)
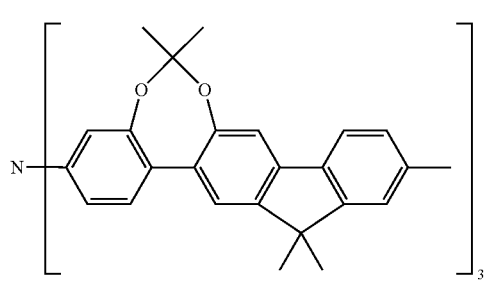(60)
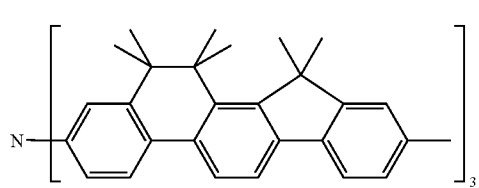(61)
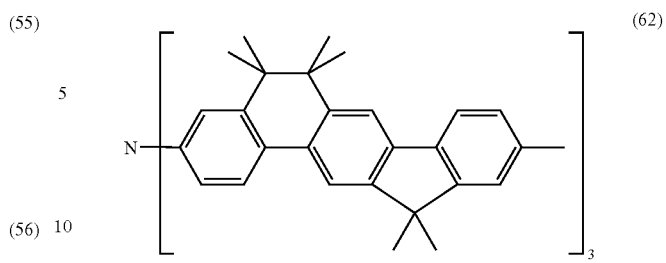(62)
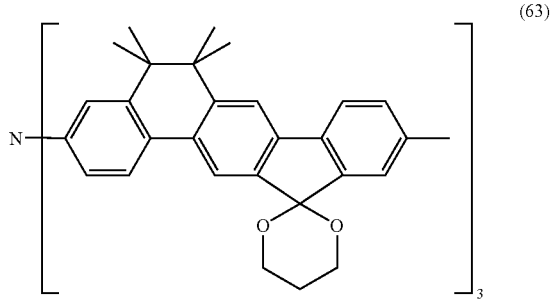(63)
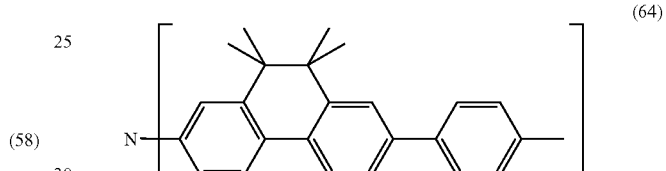(64)
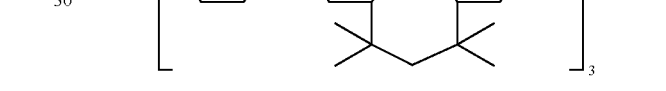(65)
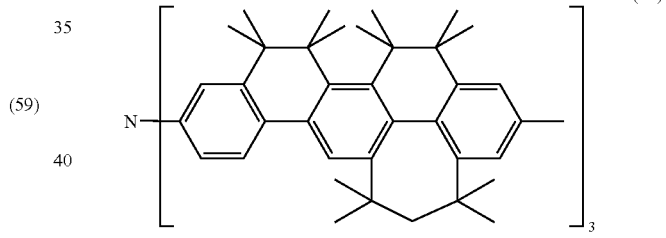(66)
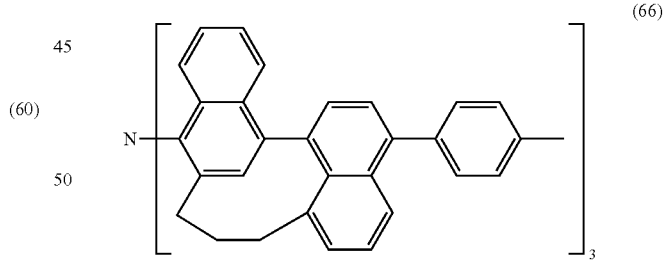(67)
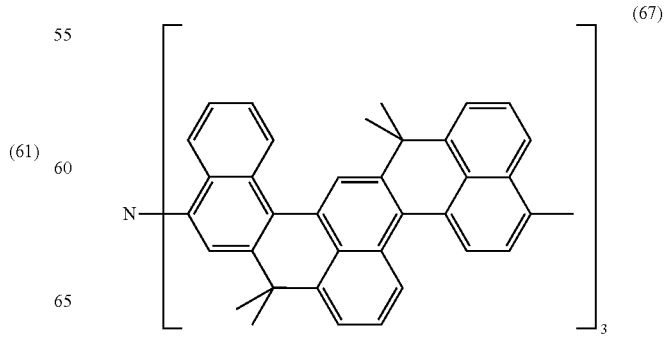

(68) 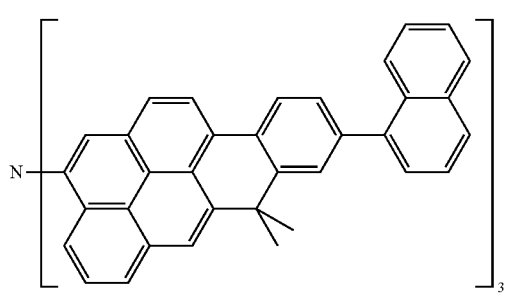
(69) 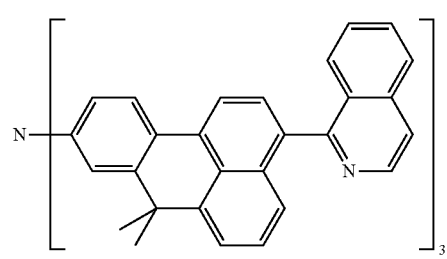
(70) 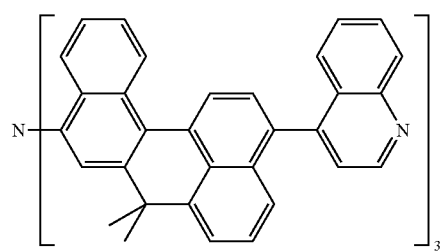
(71) 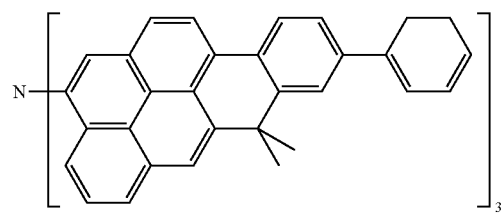
(72) 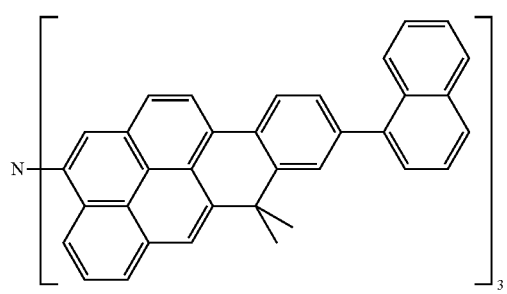
(73) 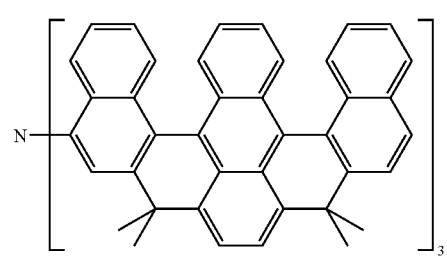
(74) 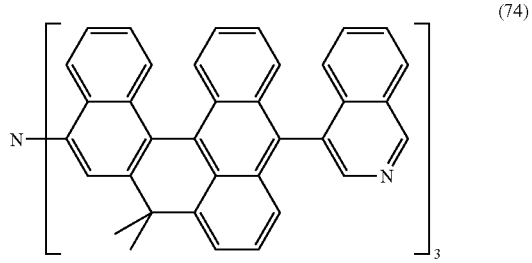
(75) 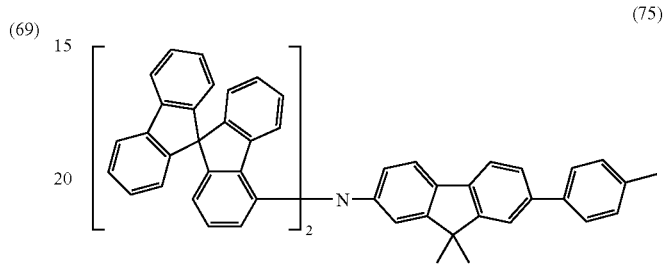
(76) 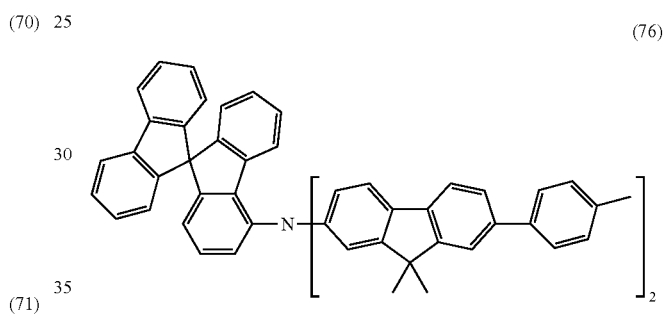
(77) 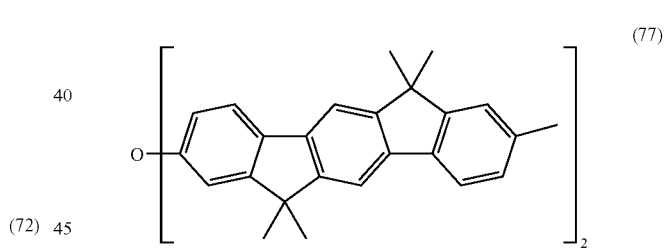
(78) 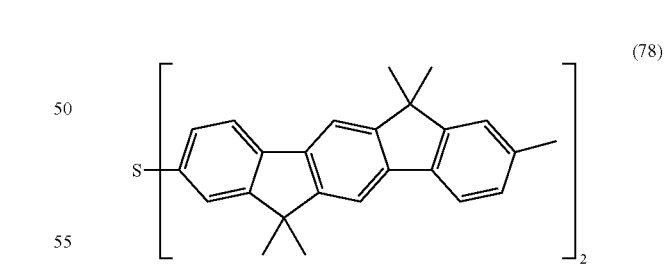
(79) 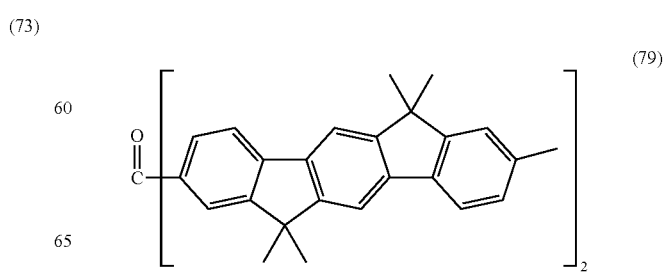

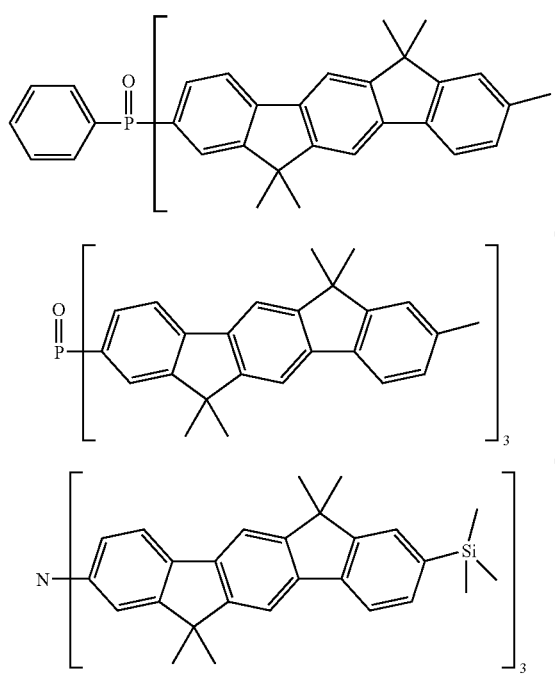

The above-described compounds according to the invention, for example compounds of the structures (8), (28) and (53), can be used, for example, as comonomers for the preparation of corresponding conjugated, partially conjugated or non-conjugated polymers, oligomers, or also as the core of dendrimers. The polymerisation here is preferably carried out via the halogen functionality.

Thus, they can be polymerised, inter alia, into soluble polyfluorenes (for example in accordance with EP 842208 or WO 00/22026), polyspirobifluorenes (for example in accordance with EP 707020, EP 894107 or EP 04028865.6), poly-para-phenylenes (for example in accordance with WO 92/18552), polycarbazoles (for example in accordance with WO 04/070772 and WO 04/113468), polyvinylcarbazoles, polythiophenes (for example in accordance with EP 1028136), polydihydrophenanthrenes (for example in accordance with WO 05/014689), polyindenofluorenes (for example in accordance with WO 04/041901 and WO 04/113412), polyketones (for example in accordance with WO 05/040302) or also into copolymers comprising a plurality of these units.

The invention thus furthermore relates to conjugated, partially conjugated and non-conjugated polymers, oligomers or dendrimers comprising one or more compounds of the formula (1), where one or more bonds from the compound of the formula (1) to the polymer or dendrimer are present.

The compounds according to the invention can be prepared by synthetic steps known to the person skilled in the art, such as, for example, bromination, Suzuki coupling, Hartwig-Buchwald coupling, etc.

Thus, the indenofluorene precursors can be prepared, for example, as shown in synthesis scheme 1: Suzuki coupling of a benzeneboronic acid and 1,4-dibromo-2,5-bis(methylcarboxylate)benzene, followed by ring closure under the action of a strong acid and reduction gives the unsubstituted trans-indenofluorene, which can be alkylated using alkylating agents. This can be selectively monobrominated by stoichiometric reaction with a brominating agent or converted into the corresponding amino compound by nitration and reduction. Tris(indenofluorenyl)amine can be synthesised by Hartwig-Buchwald coupling of the monobromo and amino compounds, as shown in synthesis scheme 2. Asymmetrical bis(indenofluorenyl)arylamines can likewise be prepared by Hartwig-Buchwald coupling, as shown in synthesis scheme 3. Tris(indenofluorenyl)phosphines or -phosphine oxides can be synthesised from monobromoindenofluorine by lithiation and reaction with $PCl_3$, as shown in synthesis scheme 4. Oxidation then gives the corresponding phosphine oxide. Other electrophiles, such as, for example, $AsCl_3$, $arylPCl_2$, $SOCl_2$, $Ar_2S_2$, etc., can likewise be employed here. Further compounds according to the invention can be synthesised in accordance with these and similar synthesis schemes by processes which are known to the person skilled in the art of organic synthesis. The resultant compounds can furthermore be brominated by standard methods and can thus be employed as monomers for polymers, oligomers or dendrimers.

Synthesis Scheme 1: Precursors of indenofluorene derivatives

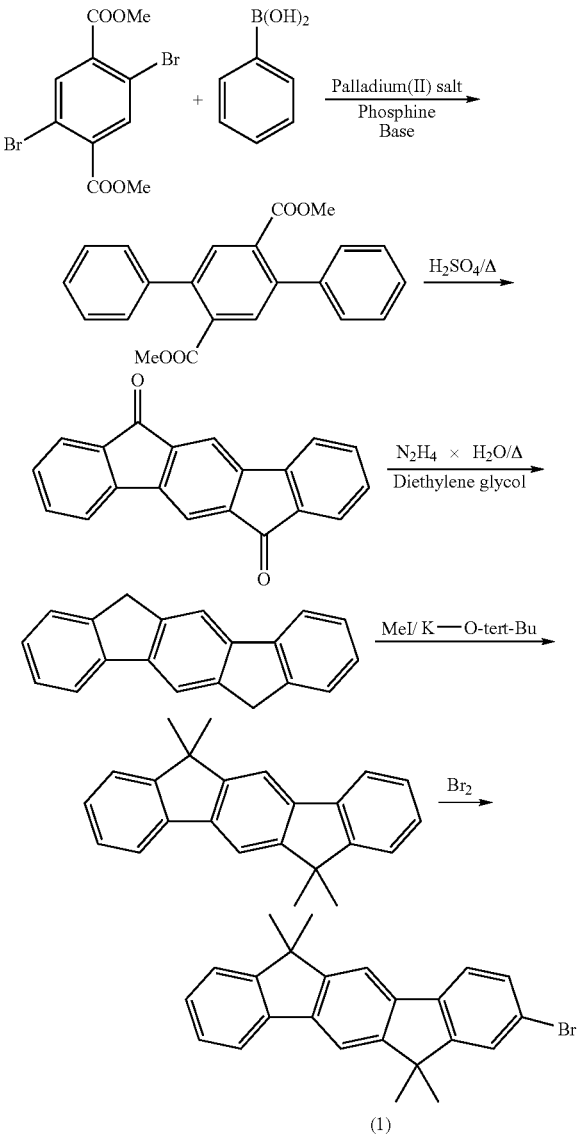

-continued
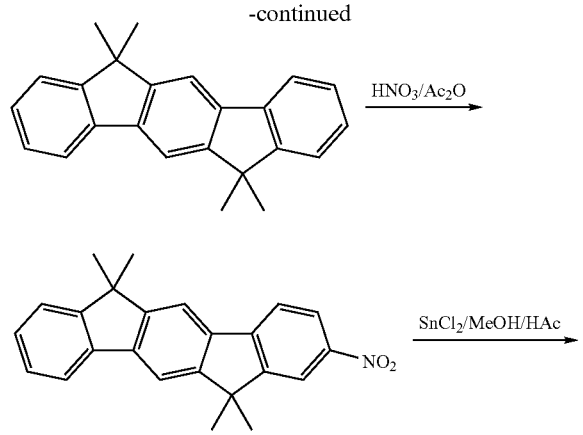
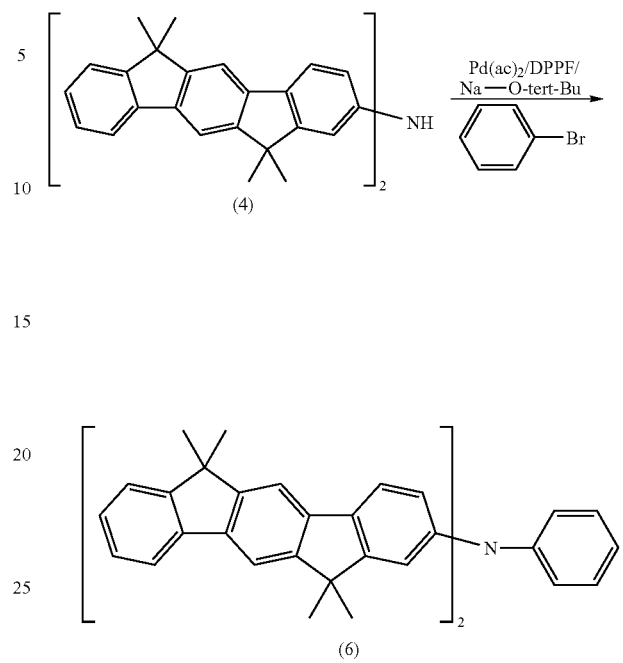
Synthesis Scheme 3: Indenofluorene-amine compounds
Synthesis Scheme 2: Indenofluorene-amine compounds
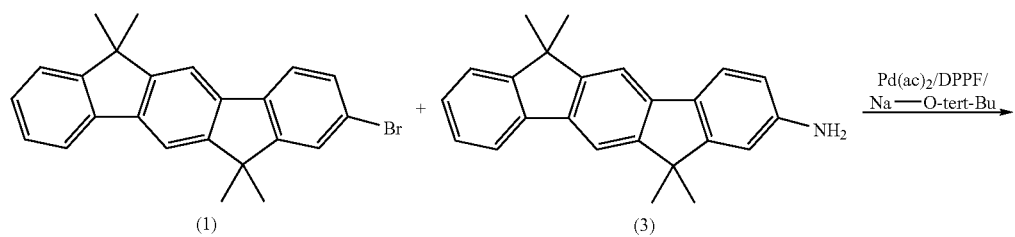
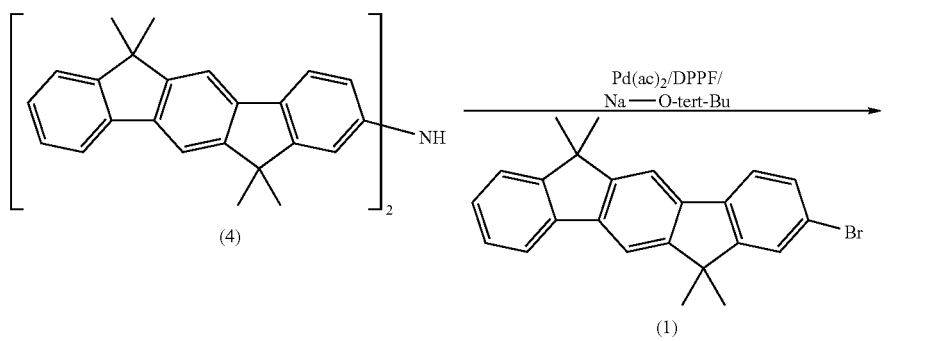
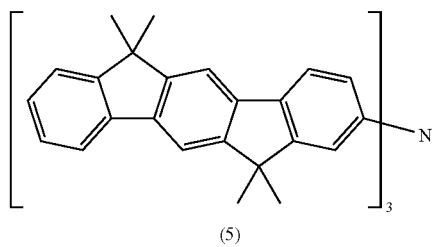

Synthesis Scheme 4: Indenofluorene-phosphine compounds

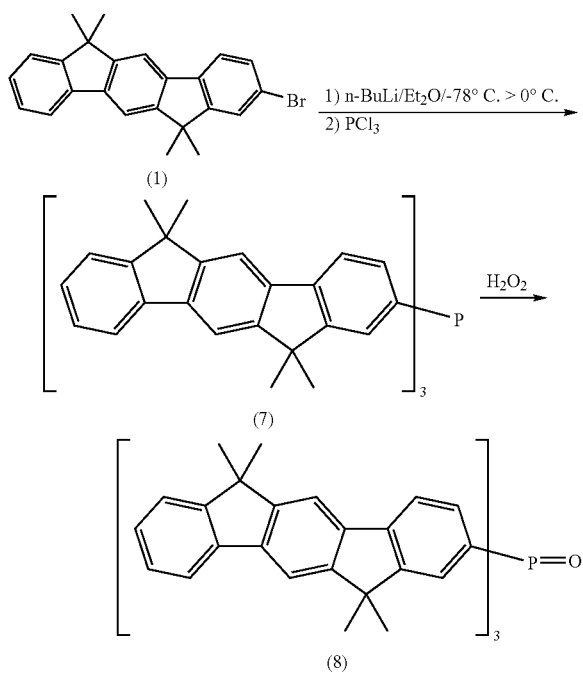

Electrophiles which can be reacted analogously:
$AsCl_3$, $SbCl_3$, $BiCl_3$, $arylPCl_2$, $aryl_2PCl$, $SCl_2$, $SOCl_2$, $SO_2Cl_2$, $Ar_2S_2$, $Ar_2Se_2$, $Ar_2Te_2$, etc.

The compounds of the formula (1) can be employed in organic electroluminescent devices, where the compound is preferably employed in the emitting layer as a mixture with at least one host material. It is preferred for the compound of the formula (1) to be the emitting compound (the dopant) in the mixture. Preferred host materials are organic compounds whose emission is of shorter wavelength than that of the compound of the formula (1) or which do not emit at all.

The invention therefore furthermore relates to mixtures comprising at least one compound of the formula (1) and at least one host material.

If the compound of the formula (1) is employed as emitting dopant, suitable host materials are various classes of substance. Preferred host materials are selected from the classes of the oligoarylenes (for example 2, 2',7,7'-tetraphenylspirobifluorene in accordance with EP 676461 or dinaphthylanthracene), in particular the oligoarylenes containing fused aromatic groups, the oligoarylenevinylenes (for example DPVBi or spiro-DPVBi in accordance with EP 676461), the polypodal metal complexes (for example in accordance with WO 04/081017), the hole-conducting compounds (for example in accordance with WO 04/058911), the electron-conducting compounds, in particular ketones, phosphine oxides, sulfoxides, etc. (for example in accordance with WO 05/084081 or WO 05/084082) or the atropisomers (for example in accordance with the unpublished application EP 04026402.0). Particularly preferred host materials are selected from the classes of the oligoarylenes containing naphthalene, anthracene and/or pyrene or atropisomers of these compounds, the oligoarylenevinylenes, the ketones, the phosphine oxides and the sulfoxides. Very particularly preferred host materials are selected from the classes of the oligoarylenes containing anthracene and/or pyrene or atropisomers of these compounds, the phosphine oxides and the sulfoxides.

The proportion of the compound of the formula (1) in the mixture of the emitting layer is between 0.1 and 99.0% by weight, preferably between 0.5 and 50.0% by weight, particularly preferably between 1.0 and 20.0% by weight, in particular between 1.0 and 10.0% by weight. Correspondingly, the proportion of host material in the layer is between 1.0 and 99.9% by weight, preferably between 50.0 and 99.5% by weight, particularly preferably between 80.0 and 99.0% by weight, in particular between 90.0 and 99.0% by weight.

It is furthermore preferred for the compounds of the formula (1) to be employed as hole-transport material and/or hole-injection material, in particular in a hole-transport layer and/or in a hole-injection layer. This applies, in particular, if the symbol Y stands for N or P. It may be preferred here for the compound to be doped with electron-acceptor compounds, for example with $F_4$-TCNQ or with compounds as described in EP 1476881 or EP 1596445.

It is furthermore preferred for the compounds of the formula (1) to be employed as matrix material for phosphorescent emitters (triplet emitters). This applies, in particular, if the symbol Y stands for C=O, P=O, S=O or $SO_2$.

It is furthermore preferred for the compounds of the formula (1) to be employed as electron-transport material, in particular in an electron-transport layer, and/or as hole-blocking material, in particular in a hole-blocking layer, in fluorescent or phosphorescent electroluminescent devices. This applies, in particular, if the symbol Y stands for C=O, P=O, S=O or $SO_2$.

Compounds of the formula (1) can also be employed in polymers either as emitting unit, as hole-transporting unit, as electron-transporting unit or as matrix for phosphorescent units.

If the compound of the formula (1) is employed as hole-transport material in a hole-transport layer or as hole-injection material in a hole-injection layer or as electron-transport material in an electron-transport layer or as hole-blocking material in a hole-blocking layer, it may also be preferred to use a proportion of 100%, i.e. to use this compound as pure material.

Preference is furthermore given to organic electroluminescent devices, characterised in that a plurality of emitting compounds are used in the same layer or in different layers, where at least one of these compounds has a structure of the formula (1). These compounds particularly preferably have in total a plurality of emission maxima between 380 nm and 750 nm, overall resulting in white emission, i.e. in addition to the compound of the formula (1), at least one further emitting compound, which may be fluorescent or phosphorescent and emits yellow, orange or red light, is also used. Particular preference is given to three-layer systems, where at least one of these layers comprises a compound of the formula (1) and where the layers exhibit blue, green and orange or red emission (for the basic structure, see, for example, WO 05/011013).

In addition to cathode, anode and the emitting layer, the organic electroluminescent device may also comprise further layers. These may be, for example: hole-injection layer, hole-transport layer, electron-transport layer and/or electron-injection layer. However, it should be pointed out at this point that each of these layers does not necessarily have to be present. Thus, in particular on use of compounds of the formula (1) with electron-conducting host materials, very good results are furthermore obtained if the organic electroluminescent device does not comprise a separate electron-transport layer and the emitting layer is directly adjacent to the electron-injection layer or to the cathode. Alternatively, the host material may also simultaneously serve as electron-transport material in an electron-transport layer. It may likewise be preferred for the organic electroluminescent device not to comprise a separate hole-transport layer and for the emitting layer to be directly adjacent to the hole-injection layer or to the anode. It may furthermore be preferred for identical or different compounds of the formula (1) to be used simultaneously as dopant in the emitting layer and as hole-conducting compound (as pure substance or as a mixture) in a hole-transport layer and/or as electron-conducting compound in an electron-transport layer.

Preference is furthermore given to an organic electroluminescent device, characterised in that one or more layers are coated by a sublimation process. The materials here are vapour-deposited in vacuum sublimation units at a pressure of below $10^{-5}$ mbar, preferably below $10^{-6}$ mbar, particularly preferably below $10^{-7}$ mbar.

Preference is likewise given to an organic electroluminescent device, characterised in that one or more layers are coated by the OVPD (organic vapour phase deposition) process or with the aid of carrier-gas sublimation. The materials here are applied at a pressure between $10^{-5}$ mbar and 1 bar.

Preference is furthermore given to an organic electroluminescent device, characterised in that one or more layers are produced from solution, such as, for example, by spin coating, or by any desired printing process, such as, for example, screen printing, flexographic printing or offset printing, but particularly preferably LITI (light induced thermal imaging, thermal transfer printing) or ink-jet printing. Soluble compounds of the formula (1) are necessary for this purpose. High solubility can be achieved by suitable substitution of the compounds.

The compounds according to the invention have the following surprising advantages over the prior art on use in organic electroluminescent devices:

1. The efficiency of corresponding devices is higher compared with systems in accordance with the prior art. This applies, in particular, on use of compounds of the formula (1) as emitters for systems which emit in dark blue.
2. The stability of corresponding devices is higher compared with systems in accordance with the prior art, which is particularly evident in a significantly longer lifetime.
3. The compounds can be sublimed well and without considerable decomposition, are consequently easier to process and are therefore more suitable for use in OLEDs than materials in accordance with the prior art. The higher thermal stability may possibly be attributable to the absence of olefinic double bonds.
4. If the compounds are employed in a hole-injection or hole-transport layer or in an electron-transport layer, the organic electroluminescent devices do not exhibit any dependence on the layer thickness of the corresponding layer. In particular, the operating voltage and the power efficiency remain unchanged, even at large layer thicknesses. This property is of major industrial importance for the production of full-colour displays.

In the present application text and also in the examples following below, the aim is the use of the compounds according to the invention in relation to OLEDs and the corresponding displays. In spite of this restriction of the description, it is readily possible for the person skilled in the art, without an inventive step, also to use the compounds according to the invention for further uses in other electronic devices, for example for organic field-effect transistors (O-FETs), organic thin-film transistors (O-TFTs), organic light-emitting transistors (O-LETs), organic integrated circuits (O-ICs), organic solar cells (O-SCs), organic field-quench devices (O-FQDs), light-emitting electrochemical cells (LECs), organic photoreceptors or also organic laser diodes (O-lasers), to mention but a few applications. The present invention likewise relates to the use of the compounds according to the invention in the corresponding devices and to these devices themselves.

The invention is explained in greater detail by the following examples, without wishing to be restricted thereby.

EXAMPLES

Unless indicated otherwise, the following syntheses are carried out under a protective-gas atmosphere. The starting materials were purchased from ALDRICH (palladium(II) acetate, tri-tert-butylphosphine, inorganic compounds, solvents). 6,12-Dihydro[1,2b]indenofluorene can be prepared by the method of Hadizad et al., *Org. Lett.* 2005, 7(5), 795-797, [1,2b]indeno-fluoren-6,12-dione can be prepared by the method of Deuschel et al., *Helv. Chimica Acta* 1951, 34, 2403, and 2-bromo-4,4'-di-tert-butylbiphenyl can be prepared by the method of Tashiro et al. *J. Org. Chem.* 1979, 44(17), 3037.

Example 1

Tris-2-(8-ethyl-6,6,12,12-tetramethyl-6,12-dihydroindeno-[1,2b]fluoren-2-yl)amine a) 6,6,12,12-Tetramethyl-6,12-dihydroindeno[1,2b]fluorene

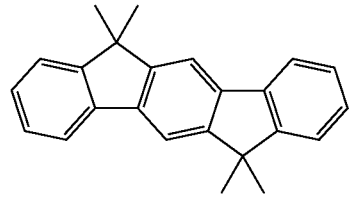

The preparation is carried out analogously to the preparation of 9,9-dimethylfluorene from 6,12-dihydroindeno[1,2b]fluorene, dimethyl sulfate and sodium hydroxide solution in accordance with JP 08113542. Yield 86.0% of theory; purity 98% according to $^1$H-NMR.

b) 2-Acetyl-6,6,12,12-tetramethyl-6,12-dihydroindeno[1,2b]fluorene

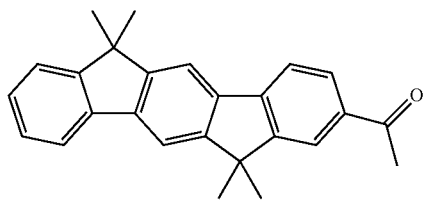

7.8 ml (110 mmol) of acetyl chloride are added dropwise to a suspension of 16.0 g (120 mmol) of aluminium chloride in 500 ml of 1,2-dichloroethane. A solution of 31.1 g (100 mmol) of 6,6,12,12-tetramethyl-6,12-dihydroindeno[1,2b]fluorene in 500 ml of 1,2-dichloroethane is added dropwise to this mixture. The mixture is subsequently stirred at room temperature for a further 4 h, poured into a mixture of 1000 g of ice and 200 ml of 2N hydrochloric acid with vigorous stirring, and the precipitated solid is filtered off with suction. The solid is washed three times with 500 ml of water and then three times with 200 ml of ethanol and dried under reduced pressure. Yield: 31.1 g (88 mmol), 88.3% of theory; purity: 98% according to ¹H-NMR.

c) 2-Ethyl-6,6,12,12-tetramethyl-6,12-dihydroindeno [1,2b]fluorene

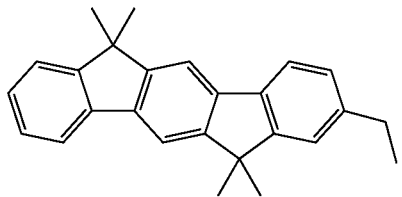

23.3 ml (480 mmol) of hydrazine hydrate are added to a suspension of 28.2 g (80 mmol) of 2-acetyl-6,6,12,12-tetramethyl-6,12-dihydroindeno-[1,2b]fluorene in 300 ml of diethylene glycol, and the mixture is refluxed for 24 h. After cooling, 300 ml of 5% hydrogen peroxide are added dropwise, and the mixture is stirred at room temperature for 16 h. The colourless solid is filtered off with suction, washed three times with 300 ml of water and three times with 200 ml of ethanol and dried under reduced pressure. Yield: 25.9 g (76 mmol), 95.7% of theory; purity: 97% according to ¹H-NMR.

d) 2-Bromo-8-ethyl-6,6,12,12-tetramethyl-6,12-dihydroindeno[1,2b]-fluorene

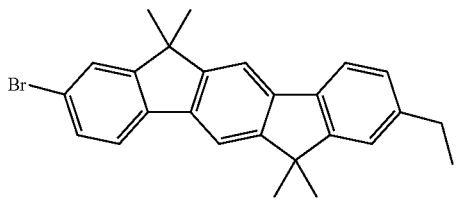

A mixture of 1.7 ml (32 mmol) of bromine and 20 ml of dichloromethane is added dropwise with exclusion of light to a solution of 10.2 g (30 mmol) of 2-ethyl-6,6,12,12-tetramethyl-6,12-dihydroindeno[1,2b]fluorene in 300 ml of dichloromethane. After the mixture has been stirred at room temperature for 16 h, 200 ml of ethanol and then 50 ml of saturated sodium sulfite solution are added. The colourless solid is filtered off with suction, washed three times with 200 ml of water and three times with 100 ml of ethanol, dried under reduced pressure and then recrystallised twice from DMF. Yield: 10.4 g (25 mmol), 83.0% of theory; purity: 97% according to ¹H-NMR.

e) 2-Ethyl-8-nitro-6,6,12,12-tetramethyl-6,12-dihydroindeno[1,2b]-fluorene

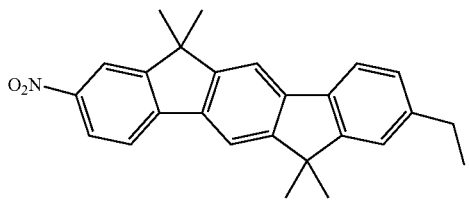

A mixture of 4 ml of 100% nitric acid and 5 ml of conc. sulfuric acid is added dropwise with exclusion of light to a vigorously stirred suspension, cooled to 0° C., of 10.2 g (30 mmol) of 2-ethyl-6,6,12,12-tetramethyl-6,12-dihydroindeno [1,2b]fluorene in 100 ml of dichloromethane. After the mixture has been stirred at room temperature for 3 h, 200 ml of water are added. The yellow solid is filtered off with suction, washed three times with 200 ml of water and three times with 100 ml of ethanol, dried under reduced pressure and then recrystallised twice from o-dichlorobenzene. Yield: 10.8 g (28 mmol), 93.7% of theory; purity: 98% according to ¹H-NMR.

f) 2-Amino-8-ethyl-6,6,12,12-tetramethyl-6,12-dihydroindeno[1,2b]-fluorene

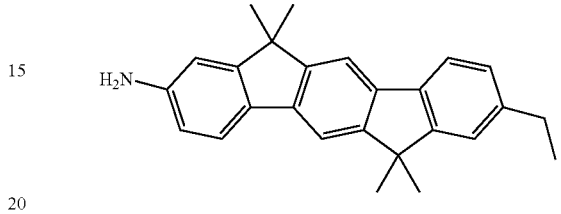

4.9 ml (100 mmol) of hydrazine hydrate and then 300 mg of freshly prepared Raney nickel are added to a vigorously stirred, refluxing suspension of 9.6 g (25 mmol) of 2-ethyl-8-nitro-6,6,12,12-tetramethyl-6,12-dihydroindeno[1,2b] fluorene in a mixture of 100 ml of toluene and 200 ml of ethanol. The mixture is left to reflux for 2 h and cooled, the solvent is removed under reduced pressure, the residue is taken up in 1000 ml of warm chloroform, the solution is filtered through silica gel, the clear solution is concentrated to 100 ml, and 300 ml of ethanol are added. After the mixture has stood for 12 h, the colourless crystals are filtered off with suction and subsequently recrystallised twice from chloroform/ethanol. Yield: 8.3 g (23.5 mmol), 93.9% of theory; purity: 98% according to ¹H-NMR.

g) Bis-2-[8-ethyl-6,6,12,12-tetramethyl-6,12-dihydroindeno[1,2b]-fluoren-8-yl]amine

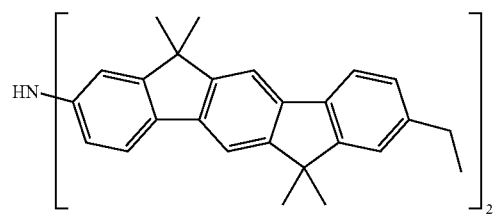

2.1 g (22 mmol) of sodium tert-butoxide, 55 mg (0.1 mmol) of 1,1'-diphenylphosphinoferrocene and 22 mg (0.1 mmol) of palladium(II) acetate are added to a suspension of 7.1 g (20 mmol) of 2-amino-8-ethyl-6,6,12,12-tetramethyl-6,12-dihydroindeno[1,2b]fluorene and 8.3 g (20 mmol) of 2-bromo-8-ethyl-6,6,12,12-tetramethyl-6,12-dihydroindeno-[1,2b]fluorene in 250 ml of toluene, and the mixture is subsequently refluxed for 16 h. After the mixture has been cooled, 250 ml of water are added, and the organic phase is separated off, filtered through silica gel and then concentrated to 30 ml. After addition of 200 ml of ethanol and standing for 16 h, the crystals are filtered off with suction and subsequently recrystallised twice from chloroform/ethanol. Yield: 9.9 g (14 mmol), 71.8% of theory; purity: 99% according to ¹H-NMR.

h) Tris-2-[8-ethyl-6,6,12,12-tetramethyl-6,12-dihydroindeno[1,2b]-fluoren-8-yl]amine

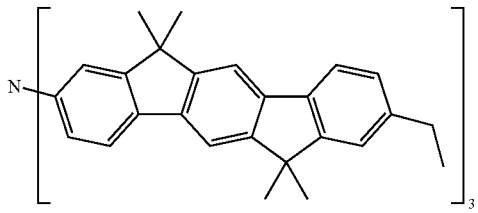

1.2 g (12 mmol) of sodium tert-butoxide, 23.5 mg (0.13 mmol) of di-tert-butylchlorophosphine and 22.4 mg (0.1 mmol) of palladium(II) acetate are added to a suspension of 6.9 g (10 mmol) of bis[2-ethyl-6,6,12,12-tetramethyl-6,12-dihydroindeno[1,2b]fluoren-8-yl]amine and 4.2 g (10 mmol) of 2-bromo-8-ethyl-6,6,12,12-tetramethyl-6,12-dihydroindeno[1,2b]fluorene in 200 ml of toluene, and the mixture is subsequently refluxed for 16 h. After the mixture has been cooled, 300 ml of water are added, and the organic phase is separated off, filtered through silica gel and then concentrated to 30 ml. After addition of 200 ml of ethanol and standing for 16 h, the crystals are filtered off with suction, subsequently recrystallised seven times from DMF and then sublimed under reduced pressure ($p=1\times10^{-5}$ mbar, T=390° C.). Yield: 5.3 g (5 mmol), 51.6% of theory; purity: 99.8% according to $^1$H-NMR.

Example 2

Bis-2-(8-ethyl-6,6,12,12-tetramethyl-6,12-dihydroindeno-[1,2b]fluoren-2-yl)ketone

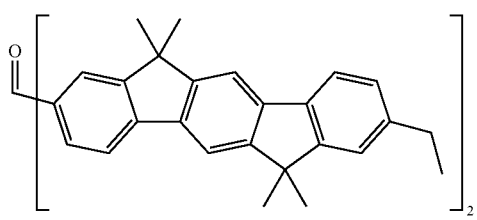

27.3 ml (41 mmol) of tert-BuLi (1.5 M in hexane) are added to a suspension, cooled to −78° C., of 8.4 g (20 mmol) of 2-bromo-8-ethyl-6,6,12,12-tetramethyl-6,12-dihydroindeno[1,2b]fluorene in 300 ml of THF, and the mixture is stirred for 8 h. 0.9 ml (10 mmol) of N,N-dimethylcarbamoyl chloride is subsequently added, the mixture is allowed to warm to room temperature and is stirred for a further 16 h, and 10 ml of acetic acid and 20 ml of water are then added. After the reaction mixture has been evaporated under reduced pressure, the residue is taken up in 200 ml of NMP, refluxed and allowed to cool to 100° C., 50 ml of water are added, the mixture is allowed to cool, and the solid is filtered off with suction and rinsed three times with 100 ml of ethanol each time. The product is subsequently recrystallised five times from NMP and then sublimed under reduced pressure ($p=1\times 10^{-5}$ mbar, T=365° C.). Yield: 4.8 g (7 mmol), 68.8% of theory; purity: 99.9% according to $^1$H-NMR.

Example 3

Tris-2-(8-ethyl-6,6,12,12-tetramethyl-6,12-dihydroindeno-[1,2b]fluoren-2-yl)phosphine oxide

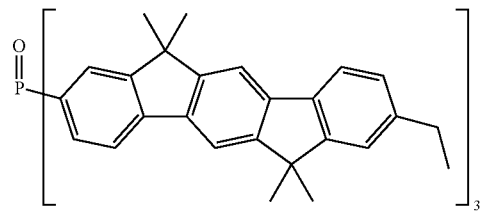

28.7 ml (43 mmol) of tert-BuLi, 1.5M in hexane, are added to a suspension, cooled to −78° C., of 8.8 g (21 mmol) of 2-bromo-8-ethyl-6,6,12,12-tetramethyl-6,12-dihydroindeno[1,2b]fluorene in 300 ml of THF, and the mixture is stirred for 8 h. 0.6 ml (7 mmol) of phosphorus trichloride is subsequently added, the mixture is allowed to warm to room temperature and is stirred for a further 16 h, and 20 ml of water are then added. After the reaction mixture has been evaporated under reduced pressure, the residue is taken up in 200 ml of chloroform, and 0.9 ml (10 mmol) of 35% hydrogen peroxide and 20 ml of water are added. The mixture is heated at 60° C. for 5 h and allowed to cool, and the solid is filtered off with suction and rinsed three times with 100 ml of water each time and three times with 100 ml of ethanol each time. The product is subsequently recrystallised five times from DMF and then sublimed under reduced pressure ($p=1\times10^{-5}$ mbar, T=395° C.). Yield: 5.4 g (5 mmol), 72.9% of theory; purity; 99.9% according to $^1$H-NMR.

Example 4

2-(Di-(4-methylphenyl)amino)-8-ethyldispiro[2,7-di-tertbutylfluoren-9,6'-indenofluoren[1,2b]fluoren-12', 9''-fluorene]

a) Dispiro[2,7-di-tert-butylfluoren-9,6'-indenofluoren[1,2b]fluoren-12',9''-fluorene]

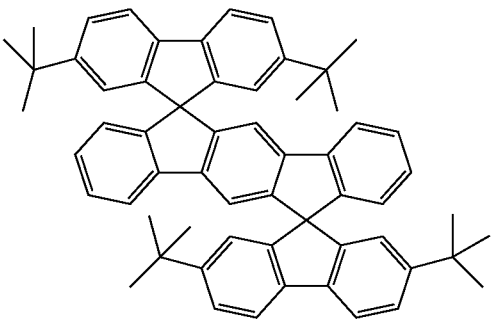

The corresponding Grignard reagent is prepared from 6.2 g (255 mmol) of magnesium and 86.3 g (250 mmol) of 2-bromo-4,4'-di-tert-butylbiphenyl in 500 ml of THF. A further 500 ml of THF and 28.8 g (100 mmol) of [1,2b]-indenofluoren-6,12-dione are added to this Grignard reagent. The reaction mixture is refluxed for 10 h and cooled, 50 ml of ethanol are added, and the mixture is evaporated to dryness under reduced pressure. The residue is refluxed for 3 h in a mixture of 1000 ml of acetic acid and 25 ml of conc. hydrochloric acid. After cooling, the colourless crystals are filtered off with suction, washed with 100 ml of acetic acid, then three times with 100 ml of ethanol each time and dried under b) 2-Acetyldispiro[2,7-di-tert-butylfluoren-9,6'-indenofluoren[1,2b]-fluoren-12',9"-fluorene]

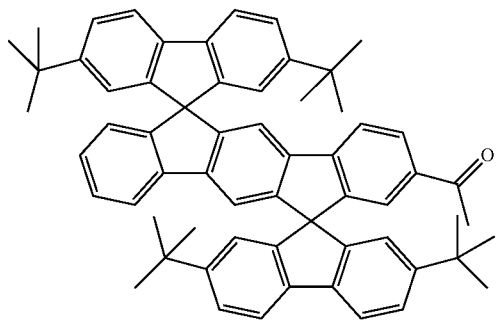

Procedure analogous to Example 1b. Instead of 6,6,12,12-tetramethyl-6,12-dihydroindeno[1,2b]fluorene, 77.9 g (100 mmol) of dispiro[2,7-di-tertbutylfluoren-9,6'-indenofluoren[1,2b]fluoren-12',9"-fluorene] are employed. Work-up: the mixture is poured with vigorous stirring into a mixture of 1000 g of ice and 200 ml of 2N hydrochloric acid, and the organic phase is separated off, washed three times with 500 ml of water and evaporated under reduced pressure. The solid is washed by stirring with 500 ml of hot ethanol, filtered off with suction, washed with 100 ml of ethanol and dried under reduced pressure. Yield: 65.0 g (79 mmol), 79.2% of theory; purity: 98% according to $^1$H-NMR.

c) 2-Ethyldispiro[2,7-di-tert-butylfluoren-9,6'-indenofluoren[1,2b]-fluoren-12',9"-fluorene]

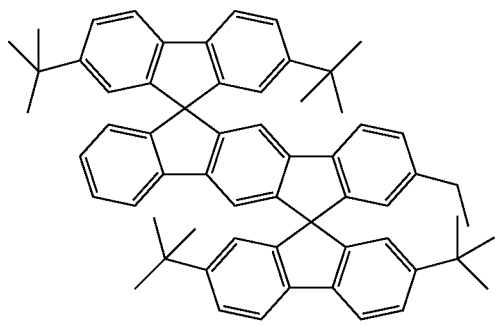

Procedure analogous to Example 1c. Instead of 2-acetyl-6,6,12,12-tetramethyl-6,12-dihydroindeno[1,2b]fluorene, 65.8 g (80 mmol) of 2-acetyldispiro[2,7-di-tert-butylfluoren-9,6'-indenofluoren[1,2b]fluoren-12',9"-fluorene] are employed. Yield: 62.2 g (77 mmol), 96.3% of theory; purity: 98% according to $^1$H-NMR.

d) 2-Bromo-8-ethyldispiro[2,7-di-tert-butylfluoren-9,6'-indenofluoren[1,2b]fluoren-12',9"-fluorene]

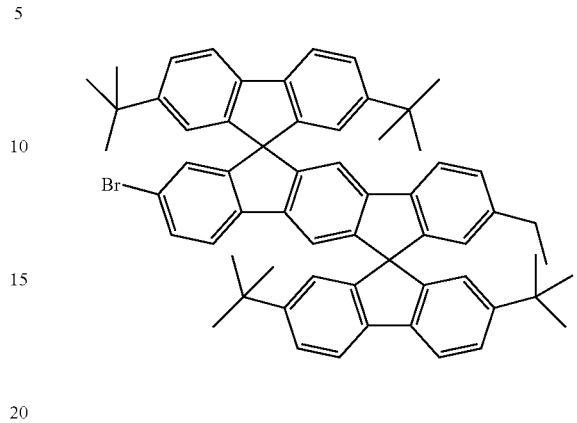

Procedure analogous to Example 1c. Instead of 2-ethyl-6,6,12,12-tetramethyl-6,12-dihydroindeno[1,2b]fluorene, 24.2 g (30 mmol) of 2-ethyldispiro[2,7-di-tert-butylfluoren-9,6'-indenofluorent[1,2b]fluoren-12',9"-fluorene] are employed. The recrystallisation is carried out from chlorobenzene. Yield: 23.3 g (26 mmol), 87.8% of theory; purity: 98% according to $^1$H-NMR.

e) 2-(Di(4-methylphenyl)amino)-8-ethyldispiro[2,7-di-tert-butylfluoren-9,6'-indenofluoren[1,2b]fluoren-12',9"-fluorene]

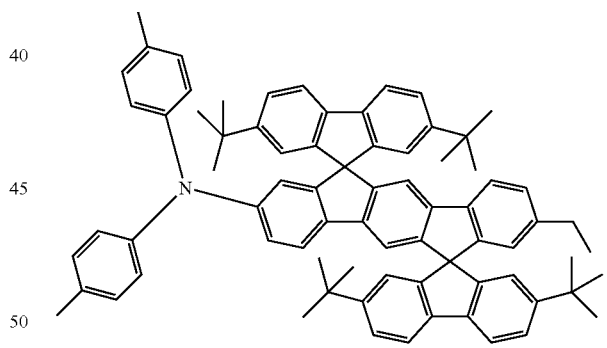

Procedure analogous to Example 1g. Instead of 2-bromo-8-ethyl-6,6,12,12-tetramethyl-6,12-dihydroindeno[1,2b]fluorene, 8.7 g (10 mmol) of 2-bromo-8-ethyldispiro[2,7-di-tert-butylfluoren-9,6'-indenofluoren[1,2b]fluoren-12',9"-fluorene] are employed, and instead of bis[2-ethyl-6,6,12,12-tetramethyl-6,12-dihydroindeno[1,2b]fluoren-8-yl]amine, 2.0 g (10 mmol) of bis(4-methylphenyl)amine are employed. The recrystallisation is carried out from chlorobenzene, and the product is subsequently sublimed under reduced pressure ($p=1\times10^{-5}$ mbar, T=410° C.). Yield: 6.0 g (6 mmol), 59.7% of theory; purity: 99.9% according to $^1$H-NMR.

Example 5

Tris-2-(8-ethyl-6,6,12,12-tetramethyl-6,12-dihydro-cis-indenofluoren-2-yl)amine

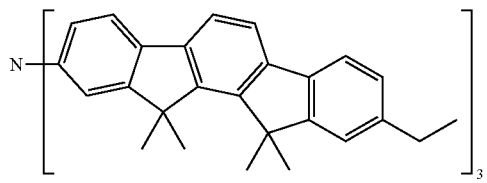

Tris-2-(8-ethyl-6,6,12,12-tetramethyl-6,12-dihydro-cis-indenofluoren-2-yl)amine can be synthesised analogously to Example 1, where cis-indenofluorene as starting compound can be synthesised in accordance with WO 04/113412.

Example 6

Bis-2-(8-ethyl-6,6,12,12-tetramethyl-6,12-dihydro-cisindenofluoren-2-yl)ketone

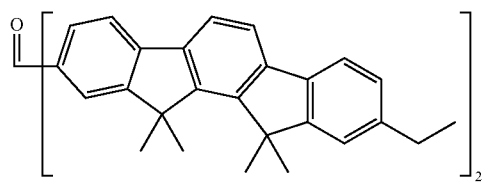

Bis-2-(8-ethyl-6,6,12,12-tetramethyl-6,12-dihydro-cis-indenofluoren-2-yl) ketone can be synthesised analogously to Example 2, where cis-indenofluorene as starting compound can be synthesised in accordance with WO 04/113412.

Example 7

Tris-2-(8-ethyl-6,6,12,12-tetramethyl-6,12-dihydro-cisindenofluoren-2-yl)phosphine oxide

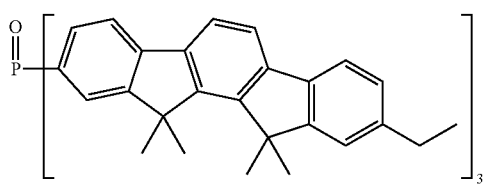

Tris-2-(8-ethyl-6,6,12,12 tetramethyl-6,12-dihydro-cis-indenofluoren-2-yl)phosphine oxide can be synthesised analogously to Example 3, where cis-indenofluorene as starting compound can be synthesised in accordance with WO 04/113412.

Example 8

Production of OLEDs with tris-2-(8-ethyl-6,6,12,12-tetramethyl-6,12-dihydroindeno[1,2b]fluoren-2-yl)amine OLEDs are produced by a general process as described in WO 04/058911, which is adapted in individual cases to the particular circumstances (for example layer-thickness variation in order to achieve optimum efficiency or colour).

In Examples 9 to 15 below, the results for various OLEDs are presented. The basic structure and the materials used (apart from the hole-transport layer) are identical in the examples for better comparability. OLEDs having the following structure are produced analogously to the above-mentioned general process:

| | |
|---|---|
| Hole-injection layer (HIL) | 20 nm PEDOT (spin-coated from water; purchased from H. C. Starck, Goslar, Germany; poly(3,4-ethylenedioxy-2,5-thiophene)) |
| Hole-transport layer (HTL) | variable layer thickness, see Table 1, tris-2-(8-ethyl-6,6,12,12-tetramethyl-6,12-dihydroindeno[1,2b]fluoren-2-yl)amine (abbreviated to HTM-1, vapour-deposited, synthesised in accordance with Example 1); |
| OR: | as comparative example 4,4',4''-tris(N-1-naphthyl-N-phenylamino)triphenylamine (abbreviated to NaphDATA, purchased from SynTec) |
| Hole-transport layer (HTL) | 30 nm NPB (N-naphthyl-N-phenyl-4,4'-diaminobiphenyl) |
| Emission layer (EML) | 30 nm, doped layer of 9,10-bis(1-naphthyl-anthracene) as host material (abbreviated to H), doped with 5% of tris[4-(2,2-diphenylvinyl)phenyl]amine as dopant (abbreviated to D, vapour-deposited, synthesised in accordance with WO 06/000388) |
| Electron conductor (ETL) | 20 nm AlQ$_3$ (purchased from SynTec, tris(quinolinato)aluminium(III)) |
| Cathode | 1 nm LiF, 150 nm Al on top. |

These OLEDs are characterised by standard methods; the electroluminescence spectra, the efficiency (measured in cd/A) and the power efficiency (measured in lm/W) are for this purpose measured as a function of the brightness, calculated from current/voltage/brightness characteristic lines (IUL characteristic lines).

Table 1 shows the results for some OLEDs (Examples 9 to 15) in which the layer thickness of the hole-transport layer (HTL) comprising tris-2-(8-ethyl-6,6,12,12-tetramethyl-6,12-dihydroindeno[1,2b]fluoren-2-yl)amine is varied. The comparative material used in the comparative examples is NaphDATA.

The host material H is 9,10-bis(1-naphthyl)anthracene, and the dopant employed is D. Both are shown below:

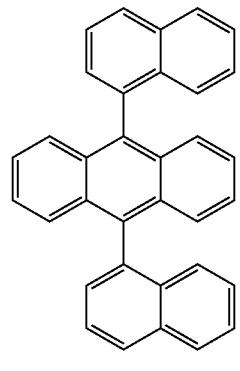

Host H

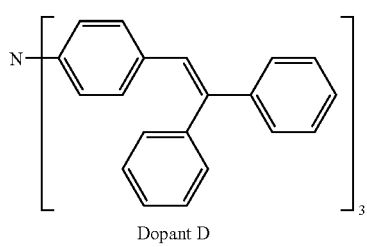

Dopant D

As can be seen from Examples 11 to 15 according to the invention in Table 1, OLEDs comprising the hole-transport material tris-2-(8-ethyl-6,6,12,12-tetramethyl-6,12-dihydroindeno[1,2b]fluoren-2-yl)amine according to the invention exhibit a significantly lower operating voltage than with NaphDATA in accordance with the prior art as hole-transport material. Furthermore, the operating voltage is independent of the layer thickness of the hole-transport layer. This property is of major advantage for the construction of full-colour displays since the thickness of the pixels of the basic colours blue, green and red can be made the same by variation of the layer thickness of the hole-transport layer. The hole-transport material according to the invention thus serves as thickness compensation layer here, without the electro-optical properties of the device being adversely affected thereby. As can be seen from the comparative examples, this is not the case for a hole-transport material (NaphDATA) in accordance with the prior art: here, a significantly higher operating voltage is required for a greater layer thickness of the hole-transport layer.

TABLE 1

| Example | HTL | Max. efficiency (cd/A) | Voltage (V) at 1000 cd/m² | CIE |
|---|---|---|---|---|
| Example 9 (comparison) | NaphDATA (30 nm) | 7.9 | 6.6 | x = 0.17; y = 0.31 |
| Example 10 (comparison) | NaphDATA (100 nm) | 7.3 | 7.7 | X = 0.16; y = 0.30 |
| Example 11 | HTM-1 (30 nm) | 7.9 | 5.8 | x = 0.16; y = 0.30 |
| Example 12 | HTM-1 (50 nm) | 7.9 | 5.8 | x = 0.16; y = 0.30 |
| Example 13 | HTM-1 (100 nm) | 8.1 | 5.7 | x = 0.16; y = 0.30 |
| Example 14 | HTM-1 (150 nm) | 8.0 | 5.9 | x = 0.16; y = 0.29 |
| Example 15 | HTM-1 (200 nm) | 7.8 | 6.0 | x = 0.16; y = 0.30 |

Example 16

Production of Phosphorescent OLEDs with bis-2-(8-ethyl-6,6,12,12-tetramethyl-6,12-dihydroindeno[1,2b]-fluoren-2-yl)ketone and tris-2-(8-ethyl-6,6,12,12-tetramethyl-6,12-dihydroindeno[1,2b]fluoren-2-yl)phosphine oxide OLEDs are produced by a general process as described in WO 04/093207, which is adapted in individual cases to the respective circumstances (for example layer-thickness variation in order to achieve optimum efficiency or colour).

The results for various OLEDs are compared here. The basic structure, such as the materials used, degree of doping and their layer thicknesses, is identical for the example experiments for better comparability. Only the matrix material in the emitter layer has been exchanged, and the examples are carried out with different triplet emitters.

Examples 17 and 18 describe comparison standards in accordance with the prior art, in which the emitter layer comprises, as matrix material, CBP or a ketone (abbreviated to ketone-1). Furthermore, OLEDs having an emitter layer consisting of the emitter materials bis-2-(8-ethyl-6,6,12,12-tetramethyl-6,12-dihydroindeno[1,2b]fluoren-2-yl)ketone and tris-2-(8-ethyl-6,6,12,12-tetramethyl-6,12-dihydroindeno[1,2b]fluoren-2-yl)phosphine oxide according to the invention are described.

OLEDs having the following structure are produced analogously to the above-mentioned general process:

| | |
|---|---|
| PEDOT | 60 nm (spin-coated from water; PEDOT purchased from H. C. Starck; poly-[3,4-ethylenedioxy-2,5-thiophene]) |
| NaphDATA | 20 nm (vapour-deposited; NaphDATA purchased from SynTec; 4,4',4''-tris(N-1-naphthyl-N-phenylamino)-triphenylamine) |
| S-TAD | 20 nm (vapour-deposited; S-TAD prepared as described in WO99/12888; 2,2',7,7'-tetrakis(diphenylamino)-spirobifluorene) |
| Emitter layer: | CBP (vapour-deposited; CBP purchased from ALDRICH and purified further, finally also sublimed twice; 4,4'-bis-(N-carbazolyl)biphenyl) (comparison standard) |
| OR: | ketone-1 (bis(9,9'-spirobifluoren-2-yl) ketone (vapour-deposited, synthesised in accordance with WO 04/093207)) (comparison standard) |
| OR: | bis-2-(8-ethyl-6,6,12,12-tetramethyl-6,12-dihydroindeno-[1,2b]fluoren-2-yl) ketone (abbreviated to M1, vapour-deposited, synthesised in accordance with Example 2), |
| OR: | tris-2-(8-ethyl-6,6,12,12-tetramethyl-6,12-dihydroindeno-[1,2b]fluoren-2-yl)phosphine oxide (abbreviated to M2, vapour-deposited, synthesised in accordance with Example 3), | in each case doped with 10% of triplet emitter E1 (synthesised in accordance with WO 05/033244), E2 (synthesised in accordance with US 2003/0068526) or E3 (synthesised in accordance with US 2003/0068526) Bathocuproine

| | |
|---|---|
| (BCP) | 10 nm (vapour-deposited; BCP purchased from ABCR, used as supplied; 2,9-dimethyl-4,7-diphenyl-1,10-phenanthroline); not used in all examples |
| AlQ₃ | 10 nm (vapour-deposited; AlQ₃ purchased from SynTec; tris(quinolinolato)aluminium(III)), not used in all examples |
| Ba/Al | 3 nm Ba, 150 nm Al on top as cathode. |

These OLEDs are characterised by standard methods; the electroluminescence spectra, the efficiency (measured in cd/A), the power efficiency (measured in lm/W) are for this purpose measured as a function of the brightness, calculated from current/voltage/brightness characteristic lines (IUL characteristic lines), and the lifetime. The lifetime is defined as the time after which the initial brightness of 1000 cd/m² has dropped to half. For an overview, the triplet emitters used and CBP and ketone-1 as comparative materials are shown below:

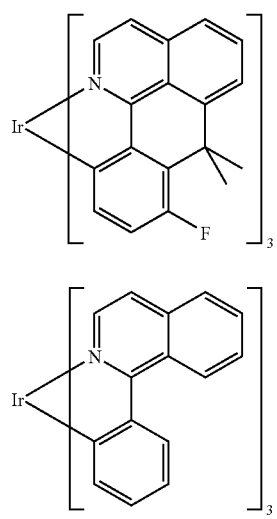
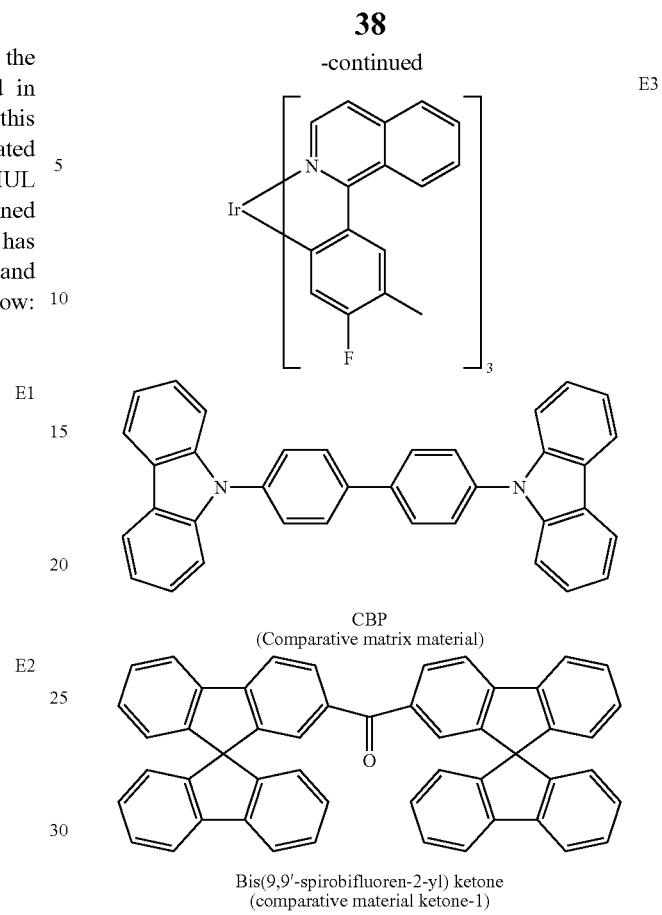

| Experiment | EML | HBL | ETL | Max. efficiency (cd/A) | Max. power efficiency (lm/W) | x, y (CIE) | Lifetime (h) at 1000 cd/cm² |
|---|---|---|---|---|---|---|---|
| Example 17 (comparison) | CBP: 15% E1 (30 nm) | BCP (10 nm) | AlQ₃ (10 nm) | 11.5 | 6.3 | 0.64, 0.36 | 2000 (extrapolated) |
| Example 18 (comparison) | Ketone-1: 15% E1 (30 nm) | BCP (10 nm) | AlQ₃ (10 nm) | 10.3 | 7.5 | 0.64, 0.36 | 12700 (extrapolated) |
| Example 19 | M1: 15% E1 (30 nm) | BCP (10 nm) | AlQ₃ (10 nm) | 18.2 | 11.5 | 0.65, 0.35 | 14000 (extrapolated) |
| Example 20 | M2: 15% E1 (30 nm) | BCP (10 nm) | AlQ₃ (10 nm) | 18.7 | 12.3 | 0.64, 0.36 | 12000 (extrapolated) |
| Example 21 | M1: 15% E1 (30 nm) | — | AlQ₃ (10 nm) | 21.7 | 14.3 | 0.65, 0.35 | 13500 (extrapolated) |
| Example 22 | M2: 15% E1 (30 nm) | — | AlQ₃ (10 nm) | 20.9 | 14.8 | 0.64, 0.36 | 11500 (extrapolated) |
| Example 23 | M1: 15% E1 (30 nm) | — | — | 23.0 | 15.7 | 0.65, 0.35 | 6000 (extrapolated) |
| Example 24 | M2: 15% E1 (30 nm) | — | — | 23.2 | 17.1 | 0.64, 0.36 | 5500 (extrapolated) |
| Example 25 (comparison) | CBP: 15% E2 (20 nm) | BCP (10 nm) | AlQ₃ (10 nm) | 6.3 | 4.7 | 0.68, 0.32 | 5000 (extrapolated) |
| Example 26 (comparison) | Ketone-1: 15% E2 (20 nm) | BCP (10 nm) | AlQ₃ (10 nm) | 8.0 | 6.0 | 0.68, 0.32 | 20000 (extrapolated) |

TABLE 2-continued

| Experiment | EML | HBL | ETL | Max. efficiency (cd/A) | Max. power efficiency (lm/W) | x, y (CIE) | Lifetime (h) at 1000 cd/cm$^2$ |
|---|---|---|---|---|---|---|---|
| Example 27 | M1: 15% E2 (20 nm) | BCP (10 nm) | AlQ$_3$ (10 nm) | 8.8 | 7.7 | 0.69, 0.31 | 22000 (extrapolated) |
| Example 28 | M2: 15% E2 (20 nm) | BCP (10 nm) | AlQ$_3$ (10 nm) | 8.5 | 7.9 | 0.68, 0.32 | 21000 (extrapolated) |
| Example 29 (comparison) | CBP: 15% E3 (20 nm) | BCP (10 nm) | AlQ$_3$ (10 nm) | 10.3 | 7.3 | 0.66, 0.34 | 4000 (extrapolated) |
| Example 30 | M1: 15% E3 (20 nm) | BCP (10 nm) | AlQ$_3$ (10 nm) | 14.6 | 12.3 | 0.67, 0.33 | 15000 (extrapolated) |
| Example 31 | M2: 15% E3 (20 nm) | BCP (10 nm) | AlQ$_3$ (10 nm) | 15.7 | 12.6 | 0.66, 0.34 | 14500 (extrapolated) |

Electroluminescence Spectra:

The OLEDs, both the comparative examples and also the OLEDs comprising M1 or M2 as matrix material, exhibit red emission with comparable colour coordinates.

Efficiency:

OLEDs produced using matrix materials M1 or M2 according to the invention exhibit both significantly better photometric efficiency and also better power efficiencies compared with matrix materials in accordance with the prior art. This applies, in particular, to the power efficiency, which is crucial from a technical point of view, due to the lower operating voltages on use of matrix materials M1 or M2.

Lifetime:

The lifetime achieved on use of matrix materials M1 or M2 according to the invention considerably exceeds that of the comparative examples with matrix material CBP and also exceeds that of the comparative examples with matrix material ketone-1.

Layer Simplification:

As can be seen from Examples 20 to 23, it is possible using matrix materials M1 and M2 according to the invention to produce OLEDs which comprise neither a hole-blocking layer nor an electron-conducting layer, without thereby impairing the overall electro-optical property profile. This is a considerable advantage in production which cannot be achieved on use of matrix materials in accordance with the prior art.

Example 32

Production of fluorescent OLEDs with bis-2-(8-ethyl-6,6,12,12-tetramethyl-6,12-dihydroindeno[1,2b]fluoren-2-yl)ketone and tris-2-(8-ethyl-6,6,12,12-tetramethyl-6,12-dihydroindeno[1,2b]fluoren-2-yl) phosphine oxide OLEDs are produced by a general process as described in WO 04/058911, which is adapted in individual cases to the particular circumstances (for example layer-thickness variation in order to achieve optimum efficiency and/or colour).

In Examples 33 to 38 below, the results for various OLEDs are presented. The basic structure and the materials used (apart from the electron-transport layer) are identical in the examples for better comparability. OLEDs having the following structure are produced analogously to the above-mentioned general process:

| | |
|---|---|
| Hole-injection layer (HIL) | 20 nm PEDOT (spin-coated from water; purchased from H. C. Starck, Goslar, Germany; poly(3,4-ethylenedioxy-2,5-thiophene)) |
| Hole-transport layer (HTL) | 50 nm, tris-2-(8-ethyl-6,6,12,12-tetramethyl-6,12-dihydroindeno[1,2b]fluoren-2-yl)amine (abbreviated to HTM-1, vapour-deposited, synthesised in accordance with Example 1) |
| Hole-transport layer (HTL) | 30 nm NPB (N-naphthyl-N-phenyl-4,4'-diaminobiphenyl) |
| Emission layer (EML) | 30 nm, doped layer of 9,10-bis(1-naphthyl-anthracene) as host material (abbreviated to H), doped with 5% of tris[4-(2,2-diphenylvinyl)phenyl]amine as dopant (abbreviated to D, vapour-deposited, synthesised in accordance with WO 06/000388) |
| Electron conductor (ETL) | bis-2-(8-ethyl-6,6,12,12-tetramethyl-6,12-dihydroindeno[1,2b]fluoren-2-yi) ketone (abbreviated to EL1, vapour-deposited, synthesised in accordance with Example 2), |
| OR: | bis-2-(8-ethyl-6,6,12,12-tetramethyl-6,12-dihydroindeno[1,2b]fluoren-2-yl)phosphine oxide, (abbreviated to EL2, vapour-deposited, synthesised in accordance with Example 3), |
| OR: | 10 nm (vapour-deposited; AlQ$_3$ purchased from SynTec; tris(quinolinolato)-aluminium(III)) |
| Cathode | 1 nm LiF, 150 nm Al on top. |

These OLEDs are characterised by standard methods; the electroluminescence spectra, the efficiency (measured in cd/A) and the power efficiency (measured in lm/W) are for this purpose measured as a function of the brightness, calculated from current/voltage/brightness characteristic lines (IUL characteristic lines).

Table 3 shows the results for some OLEDs (Examples 35 to 38) in which the electron-transport layer (ETL) consists of bis-2-(8-ethyl-6,6,12,12-tetramethyl-6,12-dihydroindeno[1,2b]fluoren-2-yl)ketone or tris-2-(8-ethyl-6,6,12,12-tetramethyl-6,12-dihydroindeno[1,2b]fluoren-2-yl)phosphine oxide. The comparative material used in the comparative examples is AlQ$_3$ in accordance with the prior art.

As can be seen from Examples 33 to 38 in Table 3, OLED devices comprising the electron-transport materials bis-2-(8-ethyl-6,6,12,12-tetramethyl-6,12-dihydroindeno[1,2b]fluoren-2-yl)ketone or tris-2-(8-ethyl-6,6,12,12-tetramethyl-6,12-dihydroindeno[1,2b]fluoren-2-yl)phosphine oxide according to the invention exhibit an operating voltage which is independent of the layer thickness. This property is of major advantage for the construction of full-colour displays since the thickness of the pixels of the basic colours blue, green and red can be made the same by variation of the layer thickness of the electron-transport layer. The electron-transport material according to the invention thus serves as thickness compensation layer here, without the electro-optical properties of the device being adversely affected thereby. As can be seen from the comparative examples, this is not the case for an electron-transport material $AlQ_3$ in accordance with the prior art.

TABLE 3

| Example | ETL | Max. efficiency (cd/A) | Voltage (V) at 1000 cd/m² | CIE |
|---|---|---|---|---|
| Example 33 (comparison) | AlQ₃ (10 nm) | 7.9 | 5.8 | x = 0.16; y = 0.30 |
| Example 34 (comparison) | AlQ₃ (30 nm) | 6.2 | 6.6 | x = 0.16; y = 0.33 |
| Example 35 | EL-1 (10 nm) | 7.8 | 5.4 | x = 0.16; y = 0.27 |
| Example 36 | EL-1 (30 nm) | 8.2 | 5.5 | x = 0.16; y = 0.27 |
| Example 37 | EL-2 (10 nm) | 8.0 | 5.2 | x = 0.16; y = 0.27 |
| Example 38 | EL-2 (30 nm) | 8.3 | 5.3 | x = 0.16; y = 0.28 |

Example 39

Production of OLEDs with 2-(di(4-methylphenyl)amino)-8-ethyldispiro[2,7-di-tert-butylfluoren-9,6'-indenofluoren-[1,2b]fluoren-12',9''-fluorene]

OLEDs are produced by a general process as described in WO 04/058911, which is adapted in individual cases to the particular circumstances (for example layer-thickness variation in order to achieve optimum efficiency and/or colour).

In Examples 40 to 42 below, the results for various OLEDs are presented. The basic structure and the materials used (apart from the emitting layer) are identical in the examples for better comparability. OLEDs having the following structure are produced analogously to the above-mentioned general process:

| Hole-injection layer (HIL) | 20 nm PEDOT (spin-coated from water; purchased from H. C. Starck, Goslar, Germany; poly(3,4-ethylenedioxy-2,5-thiophene)) |
| --- | --- |
| Hole-transport layer (HTL) | 50 nm, tris-2-(8-ethyl-6,6,12,12-tetramethyl-6,12-dihydroindeno[1,2b]fluoren-2-yl)amine (abbreviated to HTM-1, vapour-deposited, synthesised in accordance with Example 1) |
| Hole-transport layer (HTL) | 30 nm NPB (N-naphthyl-N-phenyl-4,4'-diaminobiphenyl) |
| Emission layer (EML) | 30 nm, doped layer of 9,10-bis(1-naphthylanthracene) as host material (abbreviated to H), doped with x%, see table, of 2-(di-(4-methylphenyl)amino)-8-ethyl-dispiro[2,7-di-tert-butylfluoren-9,6'-indenofluoren[1,2b]fluoren-12',9''-fluorene] as dopant (abbreviated to D, vapour-deposited, synthesised in accordance with Example 4) |
| Electron conductor (ETL) | 20 nm bis-2-(8-ethyl-6,6,12,12-tetramethyl-6,12-dihydroindeno[1,2b]fluoren-2-yl) ketone (abbreviated to EL1, vapour-deposited, synthesised in accordance with Example 2), |
| Cathode | 1 nm LiF, 150 nm Al on top. |

These OLEDs are characterised by standard methods; the electroluminescence spectra, the efficiency (measured in cd/A) and the power efficiency (measured in lm/W) are for this purpose measured as a function of the brightness, calculated from current/voltage/brightness characteristic lines (IUL characteristic lines).

Table 4 shows the results for some OLEDs (Examples 40 to 42) in which 2-(di-(4-methylphenyl)amino)-8-ethyldispiro[2,7-di-tert-butylfluoren-9,6'-indenofluoren[1,2b]fluoren-12',9''-fluorene] is used as dark-blue emitter and whose degree of doping is varied.

The host material H is 9,10-bis(1-naphthyl)anthracene, shown below:

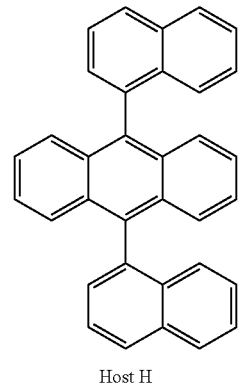

Host H

As can be seen from Examples 40 to 42 in Table 1, OLEDs comprising the dopant 2-(di-(4-methylphenyl)amino)-8-ethyldispiro[2,7-di-tert-butylfluoren-9,6'-indenofluoren[1,2b]fluoren-12',9''-fluorene] according to the invention exhibit efficient dark-blue emission

TABLE 4

| Example | EML | Max. efficiency (cd/A) | Voltage (V) at 1000 cd/m² | CIE |
|---|---|---|---|---|
| Example 40 | H 2% D | 2.3 | 6.8 | x = 0.10; y = 0.05 |
| Example 41 | H 5% D | 2.4 | 6.7 | x = 0.10; y = 0.07 |
| Example 42 | H 10% D | 2.6 | 6.5 | x = 0.11; y = 0.08 |

The invention claimed is:
1. A compound of formula (1)

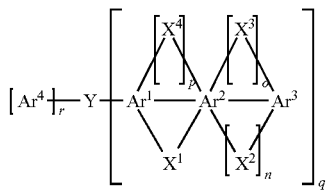

Formula 1 wherein
Y is on each occurrence N, P, P=O, C=O, O, S, S=O, or SO$_2$;
Ar$^1$ is, identically or differently on each occurrence, an aryl or heteroaryl group having 5 to 16 aromatic ring atoms, optionally substituted by one or more R$^1$;
Ar$^2$ is, identically or differently on each occurrence, an aryl or heteroaryl group selected from the group consisting of benzene, naphthalene, phenanthrene, pyridine, and thiophene, each of which is optionally substituted with one or two radicals R$^1$;
Ar$^3$ is, identically or differently on each occurrence, an aryl or heteroaryl group having 5 to 16 aromatic ring atoms, optionally substituted by one or more R$^1$, wherein said heteroaryl group is selected from the group consisting of pyridine and thiophene;
Ar$^4$ is, identically or differently on each occurrence, an aromatic or heteroaromatic ring system having 5 to 40 aromatic ring atoms, optionally substituted by one or more R$^1$;
R$^1$ is, identically or differently on each occurrence, H, F, Cl, Br, I, CN, NO$_2$, Si(R$^2$)$_3$, a straight-chain alkyl, alkoxy, or thioalkoxy group having up to 40 C atoms optionally substituted by one or more R$^2$, or a branched or cyclic alkyl, alkoxy or thioalkoxy group having 3 to 40 C atoms, optionally substituted by one or more R$^2$, wherein one or more non-adjacent CH$_2$ groups are optionally replaced by —R$^2$C=CR$^2$—, —C≡C—, Si(R$^2$)$_2$, Ge(R$^2$)$_2$, Sn(R$^2$)$_2$, C=O, C=S, C=Se, C=NR$^2$, —O—, —S—, or —CONR$^2$—, and wherein one or more H atoms is optionally replaced by F, Cl, Br, I, CN, NO$_2$, an aromatic or heteroaromatic ring system having 5 to 40 aromatic ring atoms, optionally substituted by one or more R$^2$, or an aryloxy or heteroaryloxy group having 5 to 40 aromatic ring atoms, optionally substituted by one or more R$^2$, or a combination of these systems; and wherein two or more R$^1$ optionally define a mono- or polycyclic aliphatic ring system;
R$^2$ is, identically or differently on each occurrence, H or an aliphatic or aromatic hydrocarbon radical having up to 20 C atoms;
X$^1$ and X$^4$
are, identically or differently on each occurrence, bridges which, with Ar$^1$ and Ar$^2$, define a cyclic system, and are selected from C(R$^1$)$_2$, C=O, O, S, S=O, SO$_2$, N(R$^1$), or B(R$^1$), or a combination of two, three, or four of these groups;
X$^2$ and X$^3$
are, identically or differently on each occurrence, X$^1$ and, with Ar$^2$ and Ar$^3$, define a cyclic ring system;
n, o, and p
are, identically or differently on each occurrence, 0 or 1, with the proviso that, for Y from the fifth main group, n, p and o may only simultaneously be 0 if q=3; wherein n=0 or o=0 or p=0 here means that two H atoms or R$^1$ are present instead of the bridge;
q is 1, 2, or 3, if Y is bonded via an element of the fifth main group, and is 2, if Y is bonded via oxygen, and is 1 or 2, if Y is bonded via another element of the sixth main group;
r is (3-q), if Y is bonded via an element of the fifth main group, and is (2-q), if Y is bonded via another element of the sixth main group; and
with the proviso that said compound does not include:

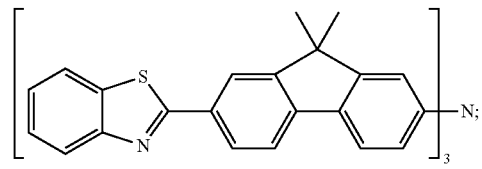

and with the proviso that when n, o, and p are simultaneously equal to 0, X$^1$ must identically be selected from the group consisting of C(R$^1$)$_2$, CO, O, S, SO, SO$_2$, NR$^1$, and BR$^1$.

2. The compound of claim 1, wherein Y is N, C=O, P, or P=O.

3. The compound of claim 1, wherein Ar$^1$ and Ar$^2$, identically or differently on each occurrence, are an aryl or heteroaryl group having 5 to 16 aromatic ring atoms, optionally substituted by one or two R$^1$ and Ar$^3$ is, identically or differently on each occurrence, an aryl or heteroaryl group having 5 to 16 aromatic ring atoms, optionally substituted by one or more wherein said heteroaryl group is selected from the group consisting of pyridine and thiophene.

4. The compound of claim 1, wherein said compound has formula (2)

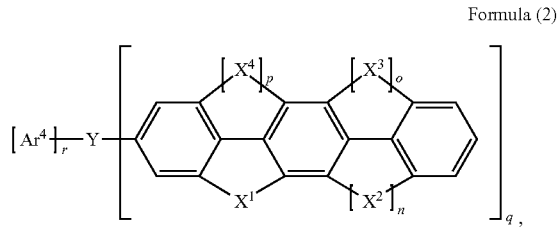

Formula (2)

wherein each of the phenyl and phenylene groups is optionally substituted by one or more R$^1$.

5. The compound of claim 1, wherein Ar$^4$, identically or differently on each occurrence, is an aromatic or hetero aromatic ring system having 5 to 16 aromatic ring atoms, optionally substituted by one or more R$^1$, or spirobifluorene, optionally substituted by one or more R$^1$.

6. The compound of claim 1, wherein R$^1$, identically or differently on each occurrence, is H, F, CN, Si(R$^2$)$_3$, a straight-chain alkyl group having up to 5 C atoms, or a branched alkyl group having 3 to 5 C atoms, wherein one or more non-adjacent CH$_2$ groups are optionally replaced by Si(R$^2$)$_2$, —R$^2$C=CR$^2$—, —C≡C—, —O—, or —S—, and wherein or more H atoms are optionally replaced by F, or a monovalent aryl or heteroaryl group having 2 to 16 C atoms, optionally substituted by one or more R$^2$.

7. The compound of claim 1, wherein X$^1$, X$^2$, X$^3$, and X$^4$, identically or differently on each occurrence, is a bridge which, with $Ar^1$ and $Ar^2$ or with $Ar^2$ and $Ar^3$, defines a cyclic system, and is selected from $C(R^1)_2$, $C=O$, $C=NR^1$, O, S, $S=O$, $SO_2$, $N(R^1)$, $P(R^1)$, $P(=O)R^1$, $C(R^1)_2-C(R^1)_2$, $C(R^1)_2-C(R^1)_2-C(R^1)_2$, $C(R^1)_2-O$, or $C(R^1)_2-O-C(R^1)_2$.

8. The compound of claim 1, wherein p=0 and wherein if n=1, o=0, and wherein if o=1, n=0.

9. The compound of claim 1, wherein q, on each occurrence, is 2 or 3, if Y is from the fifth main group and wherein q, on each occurrence, is 2, if Y is from the sixth main group.

10. The compound of claim 1, wherein said compounds have a symmetrical structure and a three-digit axis of rotation if Y is from the fifth main group and a two-digit axis of rotation if Y is from the sixth main group.

11. A conjugated, partially conjugated, or non-conjugated polymer, oligomer or dendrimer comprising one or more compounds of claim 1, wherein one or more bonds of the compound of formula (1) to said polymer, oligomer, or dendrimer are present.

12. The polymer, oligomer, or dendrimer of claim 11, wherein said polymer is selected from the group consisting of polyfluorenes, polyspirobifluorenes, poly-para-phenylenes, polycarbazoles, polyvinylcarbazoles, polythiophenes, polydihydrophenanthrenes, polyindenofluorenes, polyketones, or copolymers comprising a plurality of these units.

13. A mixture comprising at least one compound of claim 1 and at least one host material.

14. An organic electronic device comprising at least one compound of claim 1.

15. The organic electronic device of claim 14, wherein said organic electronic device is selected from the group consisting of organic electroluminescent devices, organic field-effect transistors, organic thin-film transistors, organic light-emitting transistors, organic integrated circuits, organic solar cells, organic field-quench devices, light-emitting electrochemical cells, organic photoreceptors, and organic laser diodes.

16. An organic electroluminescent device comprising anode, cathode, and at least one emitting layer, wherein said emitting layer comprises at least one compound of claim 1.

17. The organic electroluminescent device of claim 16, wherein said host material is selected from the classes of the oligoarylenes, the oligoarylenes containing fused aromatic groups, the oligoarylenevinylenes, the polypodal metal complexes, the hole-conducting compounds, the electron-conducting compounds, the ketones, the phosphine oxides, the sulfoxides, or the atropisomers.

18. The organic electroluminescent device of claim 16, wherein the proportion of the compound of claim 1 in said emitting layer is between 0.5 and 50.0% by weight, and the proportion of host material in said emitting layer is correspondingly between 50.0 and 99.5% by weight.

19. The organic electroluminescent device of claim 16, further comprising layers selected from hole-injection layers, hole-transport layers, electron-transport layers, and/or electron-injection layers.

20. An organic electroluminescent device comprising anode, cathode, at least one emitting layer, and at least one hole-transport layer and/or at least one hole-injection layer comprising at least one compound of claim 1.

21. An organic electroluminescent device comprising anode, cathode, and at least one emitting layer which comprises at least one phosphorescent emitter, wherein said emitting layer comprises, as matrix material, at least one compound of claim 1.

22. An organic electroluminescent device comprising anode, cathode, at least one emitting layer, and at least one electron-transport layer and/or at least one hole-blocking layer comprising at least one compound of claim 1.

23. The compound of claim 1, wherein $X^1$ is identically selected from the group consisting of $C(R^1)_2$, CO, O, S, SO, $SO_2$, $NR^1$, and $BR^1$.

* * * * *